(12) United States Patent
Kaneda et al.

(10) Patent No.: US 8,691,212 B2
(45) Date of Patent: Apr. 8, 2014

(54) THERAPEUTIC/PROPHYLACTIC AGENT FOR PROSTATE CANCER

(75) Inventors: Yasufumi Kaneda, Osaka (JP); Yoshifumi Kawaguchi, Osaka (JP); Toshimitsu Itai, Osaka (JP)

(73) Assignee: GenomIdea Inc., Osaka (JP)

( * ) Notice: Subject to any disclaimer, the term of this patent is extended or adjusted under 35 U.S.C. 154(b) by 0 days.

(21) Appl. No.: 13/119,148

(22) PCT Filed: Sep. 16, 2009

(86) PCT No.: PCT/JP2009/066195
§ 371 (c)(1),
(2), (4) Date: May 26, 2011

(87) PCT Pub. No.: WO2010/032764
PCT Pub. Date: Mar. 25, 2010

(65) Prior Publication Data
US 2011/0223148 A1    Sep. 15, 2011

(30) Foreign Application Priority Data
Sep. 16, 2008   (JP) .................................. 2008-237102

(51) Int. Cl.
*A61K 48/00* (2006.01)
*C12N 15/63* (2006.01)

(52) U.S. Cl.
USPC ..................................... 424/93.3; 435/320.1

(58) Field of Classification Search
None
See application file for complete search history.

(56) References Cited

U.S. PATENT DOCUMENTS

| | | | |
|---|---|---|---|
| 5,631,237 A | 5/1997 | Dzau et al. | |
| 5,843,451 A * | 12/1998 | Compans et al. | 424/192.1 |
| 6,432,925 B1 * | 8/2002 | Hoon et al. | 514/44 R |
| 6,472,375 B1 * | 10/2002 | Hoon et al. | 514/44 R |
| 6,913,923 B2 * | 7/2005 | Kaneda | 435/320.1 |
| 7,056,689 B1 | 6/2006 | Lorence et al. | |
| 7,427,395 B2 * | 9/2008 | Yamamoto et al. | 424/93.2 |
| 7,736,640 B2 | 6/2010 | Lorence et al. | |
| 7,803,621 B2 * | 9/2010 | Kaneda | 435/455 |
| 7,858,356 B2 * | 12/2010 | Kaneda et al. | 435/235.1 |
| 7,871,765 B2 * | 1/2011 | Kotani et al. | 435/5 |
| 2003/0013195 A1 * | 1/2003 | Kaneda | 435/456 |
| 2005/0239188 A1 * | 10/2005 | Kaneda | 435/235.1 |
| 2005/0250718 A1 * | 11/2005 | Sakakibara et al. | 514/44 |
| 2006/0165656 A1 | 7/2006 | Yamamoto et al. | |
| 2006/0216310 A1 | 9/2006 | Lorence et al. | |
| 2007/0287677 A1 | 12/2007 | Kaneda | |
| 2008/0014183 A1 | 1/2008 | Okano et al. | |
| 2008/0031855 A1 * | 2/2008 | Okano et al. | 424/93.6 |
| 2008/0206201 A1 | 8/2008 | Beier et al. | |
| 2008/0226674 A1 * | 9/2008 | Kotani et al. | 424/207.1 |
| 2011/0020282 A1 | 1/2011 | Beier et al. | |

FOREIGN PATENT DOCUMENTS

| | | |
|---|---|---|
| JP | 2002-06578 | 3/2002 |
| JP | 2007-020494 A | 2/2007 |
| JP | A-2008-519590 | 6/2008 |
| WO | WO94/25627 | 11/1994 |
| WO | WO 9918799 | * 4/1999 |

OTHER PUBLICATIONS

Zhu et al. Cancer Research 2006, vol. 61, pp. 3725-3734.*
Lecheleider et al. Clin. Cancer Research, Aug. 2008, vol. 14, pp. 5284-5291.*
Yonemitsa et al. Frontiers in Biosicnece, Jan 2008, vol. 13, pp. 1892-1898.*
Mima et al. Mol. Cancer Therapeutics, 2006, vol. 5(4), pp. 1021-1028.*
Suzuki et al. FEEs Apr. 2008, vol. 582, No. 9, pp. 1325-1329.*
Cole et al., "Efficient priming of CD8+ memory T cells specific for a subdominant epitope following Sendai virus infection," Journal of Immunology 158, 4301-4309, 1997.
Dzau et al., "Fusigenic viral liposome for gene therapy in cardiovascular diseases," Proc. Natl. Acad. Sci. USA, 93, 11421-11425, 1996.
International Search Report & Written Opinion, PCT/JP2009/066195, mailed Oct. 27, 2009.
Kaneda, "Development of novel cancer immunotherapy using inactivated Sendai Virus," Hematology & Oncology, 2007, vol. 55, No. 3, pp. 346-353.
Kaneda et al., "Gene therapy using HVJ-liposomes: the best of both worlds?," Molecular Medicine Today, 5, 298-303, 1999.
Ledley, "Nonviral Gene Therapy: The promise of genes as pharmaceutical products," Human Gene Therapy, vol. 6, 1129-1144, 1995.
Mulligan, "The basic science of gene therapy," Science, 260, 926-932, 1993.
Supplementary European Search Report for EP Application No. 09 81 4609, dated Sep. 28, 2012.
Kinoh et al., "Novel Oncolytic Sendai Virus Vectors Developed for Use in Gene Therapy for Prostate Cancer," 64th Annual Meeting of the Japanese Cancer Association, Aug. 15, 2005, p. 434.
Komaru et al., "Evaluation of an M Gene-Deficient Sendai Virus Vector with Selective Oncolytic Activity Targeted at Urokinase-Expressed Cancer Cells Using Prostate Cancer," Dai 72 Kai Nippon Hinyokiki Gakki Tobu Sokai Korikushu, Mar. 15, 2008, p. 426.
Kita et al., "Interferon Producing Capacities of Benign Prostatic Hypertrophy Patients and Prostatic Cancer Patients," Bulletin de L'Institute Pasteur de Kyoto 2, 9-14, 1988.

(Continued)

*Primary Examiner* — Bao Li
(74) *Attorney, Agent, or Firm* — Banner & Witcoff, Ltd.

(57) ABSTRACT

Provided are a novel therapeutic agent and therapeutic method for prostatic cancers. More specifically, a prostatic cancer therapeutic/prophylactic agent having a viral envelope vector, particularly a Sendai viral envelope vector, as an active ingredient, the therapeutic/prophylactic agent which is an apoptosis induction promoter, the therapeutic/prophylactic agent used for prostatic cancers whose androgen susceptibility has been partially or completely reduced, and a melanoma therapeutic/prophylactic agent containing a Sendai viral envelope vector as the only active ingredient, and the like are provided.

9 Claims, 13 Drawing Sheets

(56) References Cited

OTHER PUBLICATIONS

Kurooka and Kaneda, "Anti-Tumor Immunotherapy with Inactivated Sendai Virus Particles," Virus 57, 19-28, 2007.

Kinoh & Inoue, "New cancer therapy using genetically-engineered oncolytic Sendai virus vector," Front. Biosci. 13, 2327-34, 2008.

Tsuboniwa et al., "HVJ-riposome-ho o Oyo shita Zenritsusen Gan Saibo ni Taisuru Jisatsu Idenshi Ryoho no Kento," The 89th Annual Meeting of the Japanese Urological Association, Feb. 20, 2001, 322.

\* cited by examiner

THERAPEUTIC/PROPHYLACTIC AGENT FOR PROSTATE CANCER

TECHNICAL FIELD

The present invention relates to a pharmaceutical that exhibits an antitumor action in vivo (for cancer treatment). In more detail, the present invention relates to a therapeutic/prophylactic agent for the treatment of prostatic cancers, having a viral envelope, particularly the inactivated Sendai virus (Hemagglutinating Virus of Japan, hereinafter sometimes referred to as HVJ) envelope (hereinafter sometimes referred to as HVJ-E), as an active ingredient. The present invention also relates to a therapeutic/prophylactic agent for melanoma having the inactivated Sendai viral envelope as the only active ingredient.

BACKGROUND ART

Many viral methods and non-viral methods have been developed for the purpose of introducing a gene into cultured cells and living tissues for functional analyses of gene and gene therapy (non-patent documents 1 and 2). For introduction of a gene into a cell, a viral method is generally effective. However, the method using a viral vector has a safety problem because of the possibility of parental virus-derived gene introduction and its expression, immunogenicity, and the possibility of modification of host genome structure. On the other hand, many of the non-viral methods using a liposome and the like show lower cytotoxicity and lower immunogenicity than do the viral methods. However, the efficiency of the gene introduction into cultured cells and living tissues tends to be lower than with viral vectors.

"Sendai virus" is a virus belonging to the genus Paramyxovirus in the Paramyxoviridae, possessing cell fusion action. The virion of this virus has on its surface an envelope containing hemagglutinin and neuraminidase, exhibiting polymorphism with a diameter of 150 to 300 nm. Also, Sendai virus has a minus-stranded RNA about 15,500 bases long as the genome, has RNA polymerase, is unstable to heat, agglutinates almost all kinds of erythrocytes, and exhibits hemolytic nature. By inactivating this virus, a Sendai viral envelope vector that has become replication-deficient is obtained.

HVJ attracted attention for fusing Ehrlich tumor cells (non-patent document 3), and analysis of cellular membrane fusion activity (hereinafter fusion activity) has been undertaken and its use as a transgenic vector has been studied. However, HVJ has high immunogenicity and is known to induce CTL particularly when NP protein is produced in a large amount (Cole G. A. et al. Journal of Immunology 158, 4301-4309, 1997). Moreover, inhibition of synthesis of protein by a host is feared. Thus, a method of preparing fused particles (HVJ-liposome) by fusing a liposome including a gene or a protein with HVJ inactivated by ultraviolet irradiation in advance was devised, by which noninvasive gene introduction into a cell or a living organism has been enabled (patent document 1, and non-patent documents 4 and 5).

The present inventors previously developed a novel hybrid transfection vector by combining a virus having a capability of effectively delivering genes (highly efficient) and a non-viral vector with lesser cytotoxicity and immunogenicity (of low toxicity), and constructed a fusion-forming viral liposome having a fusion-forming envelope derived from the hemagglutinating virus of Japan (HVJ; Sendai virus) (Kaneda, 1998; Kaneda et al., 1999). In this delivery system, a DNA-filling liposome is fused with UV-inactivated Sendai virus to form Sendai virus-liposome (400 to 500 nm across), which is a fusion-forming virus-liposome. An advantage of fusion-mediated delivery resides in that the transfected DNA is protected against endosome lysis and lysosome lysis in receptor cells. For example, the DNA incorporated in Sendai virus-liposome can be safely delivered to mammalian cells (Patent document 2). RNAs, oligonucleotides and drugs can also be introduced into cells in vitro and in vivo efficiently. Furthermore, the present inventors invented a transfection vector having an extraneous gene enclosed therein by freeze-drying the Sendai viral envelope or mixing the same with a surfactant, as a transfection vector possessing high transfection activity that is based on a viral envelope, that is safe and stable, and that enables transfection to a broad range of biological tissues (Patent document 3). It is also possible to efficiently introduce a substance into the brain or the central nervous system using the Sendai viral envelope (Patent document 4). Furthermore, the present inventors also found a method wherein a chemotherapy agent such as an anticancer agent is enclosed in the Sendai viral envelope, and transferred into cells or a living organism, and also found that an immune adjuvant effect is obtained (Patent document 4, Patent document 5, Patent document 6).

By the way, a variety of cancer therapeutic methods have already been developed. Treatments for general cancers, particularly solid tumors, include a method wherein an effective drug is transferred to cancer tissue to kill cancer cells. Also, not only chemotherapy or medication therapy involving administration of a chemotherapy agent consisting of a low-molecular compound, but also a variety of therapies such as radiotherapy, immunotherapy, and endocrine therapy have been developed. However, the current situation remains such that it cannot be concluded that solid tumors are completely remittable diseases. Out of solid tumors, prostatic cancers, in particular, develop as cells of the prostate lose their normal cell proliferating function and self-propagate orderlessly. In recent years, the incidence and mortality rates for prostatic cancer patients in Japan have been increasing constantly.

In case of a cancer localized in the prostate, radical prostatectomy is indicated; in recent years, however, patients with early cancers judged to be surgically resectable have been increasing with the spread of screening using the prostate-specific antigen (PSA) marker. However, the frequency of recurrence after surgical resection is reportedly generally 20 to 57%, the still high recurrence rate posing a problem.

Generally, for recurrent cases and prostatic cancers with advances noted outside the prostate, topical radiation irradiation, endocrine therapy and the like are chosen as salvage therapies, but the likelihood of obtaining radical healing is generally low. Hence, neoadjuvant therapy, in which endocrine therapy is performed before surgery, is performed for the purpose of increasing the likelihood of complete resection, but the results obtained are unsatisfactory. Particularly in endocrine therapy, prostatic cancer cells that have acquired hormone refractoriness often emerge, resulting in poorer therapeutic results. For this reason, as the situation stands, there are expectations for the development of a more effective prostatic cancer therapeutic method that will substitute for preoperative endocrine therapy, and a method of efficiently treating hormone-refractory prostatic cancer.

PRIOR ART REFERENCES

Patent Documents

Patent document 1: U.S. Pat. No. 5,631,237
Patent document 2: WO2001/057204

Patent document 3: JP-A-2002-065278
Patent document 4: WO2005/095613
Patent document 5: WO2004/039406
Patent document 6: WO2005/094878

Non-Patent Documents

Non-patent document 1: Mulligan, Science, 260, 926-932, 1993
Non-patent document 2: Ledley, Human Gene Therapy, vol. 6, 1129-1144, 1995
Non-patent document 3: Cole G. A. et al. Journal of Immunology 158, 4301-4309, 1997
Non-patent document 4: Dzau et al., Proc. Natl. Acad. Sci. USA, 93, 11421-11425, 1996
Non-patent document 5: Kaneda et al., Molecular Medicine Today, 5, 298-303, 1999

SUMMARY OF THE INVENTION

Problems to be Solved by the Invention

It is a problem to be solved by the present invention to provide a novel therapeutic/prophylactic agent and therapeutic/prophylactic method for prostatic cancers. More specifically, to provide a therapeutic/prophylactic agent and therapeutic/prophylactic method for prostatic cancers, particularly for prostatic cancers that have become hormone-refractory due to endocrine therapy. It is another problem to be solved by the present invention to provide a novel therapeutic/prophylactic agent for melanoma.

Means of Solving the Problems

The present inventors conducted extensive investigations to solve the above-described problems, and found that viral envelops, particularly the Sendai viral envelope itself, induce apoptosis to tumor cells (prostatic cancer cells) to exhibit an antitumor effect, thus demonstrating that viral envelops, particularly the Sendai viral envelope itself, can be utilized as a therapeutic/prophylactic agent for prostatic cancers. The present inventors also found that Sendai viral envelope itself can be utilized as a therapeutic/prophylactic agent for melanoma. Accordingly, the present invention provides the following:

[1] a prostatic cancer therapeutic/prophylactic agent containing a viral envelope as an active ingredient;
[2] the therapeutic/prophylactic agent described in [1] above, wherein the virus is a virus belonging to any one family selected from the group consisting of Poxviridae, Herpesviridae, Hepadnaviridae, Baculoviridae, Retroviridae, Togaviridae, Coronaviridae, Flaviviridae, Paramyxoviridae, Orthomyxoviridae, Bunyaviridae, Rhabdoviridae, Arenaviridae, and Filoviridae;
[3] the therapeutic/prophylactic agent described in [2] above, wherein the virus is a virus belonging to Paramyxoviridae;
[4] the therapeutic/prophylactic agent described in [1] above, wherein the virus is selected from the group consisting of Sendai virus, retrovirus, adeno-associated virus, herpesvirus, vaccinia virus, poxvirus and influenza virus;
[5] the therapeutic/prophylactic agent described in [4] above, wherein the virus is Sendai virus;
[6] the therapeutic/prophylactic agent described in any one of [1] to [5] above, which causes the activation of NK cells or acialo GM1-positive cells or the induction of interferon α or β production from tumor cells;
[7] the therapeutic/prophylactic agent described in any one of [1] to [6] above, wherein the androgen susceptibility of the prostatic cancer has been partially or completely reduced.
[8] the therapeutic/prophylactic agent described in any one of [1] to [6] above, wherein the prostatic cancer is hormone-refractory;
[9] the therapeutic/prophylactic agent described in any one of [1] to [8] above, which is administered directly to the prostatic cancer;
[10] the therapeutic/prophylactic agent described in [9] above, which is injected directly to the prostatic cancer;
[11] the therapeutic/prophylactic agent described in any one of [1] to [10] above, which is used in combination with another cancer therapeutic method;
[12] the therapeutic/prophylactic agent described in [11] above, wherein the other cancer therapeutic method is selected from the group consisting of medication, endocrine therapy, radiotherapy, chemotherapy and immunotherapy;
[13] the therapeutic/prophylactic agent described in [12] above, which is administered to a prostatic cancer patient having a history of receiving endocrine therapy;
[14] the therapeutic/prophylactic agent described in [13] above, wherein the prostatic cancer patient having a history of receiving endocrine therapy bears a prostatic cancer whose androgen susceptibility has been partially or completely reduced;
[15] the therapeutic/prophylactic agent described in [13] above, wherein the prostatic cancer patient having a history of receiving endocrine therapy bears a hormone-refractory prostatic cancer;
[16] a method of treating/preventing prostatic cancer, comprising administering an effective amount of a viral envelope to a prostatic cancer patient or a person at a risk of contracting prostatic cancer;
[17] a viral envelope for use in the treatment/prevention of prostatic cancer;
[18] a use of a viral envelope for producing a therapeutic/prophylactic agent for prostatic cancer;
[19] an inducer of prostatic cancer cell apoptosis, comprising a viral envelope as an active ingredient;
[20] the apoptosis inducer described in [19] above, wherein the virus is Sendai virus;
[21] a method of inducing prostatic cancer cell apoptosis, comprising administering an effective amount of a viral envelope to a prostatic cancer patient or a person at a risk of contracting prostatic cancer;
[22] a viral envelope for use in inducing prostatic cancer cell apoptosis;
[23] a use of a viral envelope for producing a prostatic cancer cell apoptosis inducer;
[24] an agent for the treatment/prophylaxis of melanoma, comprising the Sendai viral envelope (HVJ-E) as the only active ingredient;
[25] the agent described in [24] above, wherein the amount administered per dose is 10 to 10000 HAU;
[26] the agent described in [24] above, wherein the amount administered per dose is 40 to 400 HAU;
[27] the agent described in [24] above, wherein the administration frequency is 1 to 10 times;
[28] the agent described in [24] above, wherein the administration frequency is 3 to 6 times;
[29] a method of treating/preventing melanoma, comprising administering an effective amount of the Sendai viral envelope (HVJ-E) as the only active ingredient for treating/preventing melanoma to a melanoma patient or a person at a risk of contracting melanoma;

[30] a pharmaceutical composition comprising the Sendai viral envelope (HVJ-E) as the only active ingredient for use in the treatment/prevention of melanoma;

[31] a use of a pharmaceutical composition comprising the Sendai viral envelope (HVJ-E) as the only active ingredient for producing a therapeutic/prophylactic agent for melanoma, and the like.

Effect of the Invention

Provided by the present invention is a novel therapeutic/prophylactic agent for prostatic cancers. The prostatic cancer therapeutic/prophylactic agent provided by the present invention contains a viral envelope, particularly the Sendai viral envelope, as an active ingredient thereof. The therapeutic/prophylactic agent of the present invention exhibits an excellent therapeutic effect particularly on hormone-refractory prostatic cancers.

In the treatment of prostatic cancers, PSA screening, surgical resection, endocrine therapy, radiothrapy and the like are currently available, but the radical treatment thereof remains a major problem. Using in vivo experiments, the present invention has shown that the Sendai viral envelope remarkably regresses a prostatic cancer when administered directly to the cancer.

Also provided by the present invention is a novel therapeutic/prophylactic agent for melanoma. The therapeutic/prophylactic agent exhibits a melanoma regression effect at low doses.

BRIEF DESCRIPTION OF THE DRAWINGS

FIG. 5(A) is a graphic representation showing changes over time in the amounts expressed of type I interferons (IFN-α, β) produced by PC3 in the medium (y-axis) versus the number of virions of the Sendai viral envelope (x-axis). The graphs show statistically processed data on the results of three runs. FIG. 5(B) is a Western blot analysis image showing the actions of the Sendai viral envelope and an anti-INF receptor antibody on the expression of RIG-I. β actin was used as the internal control.

MODES FOR EMBODYING THE INVENTION

Figure 1:
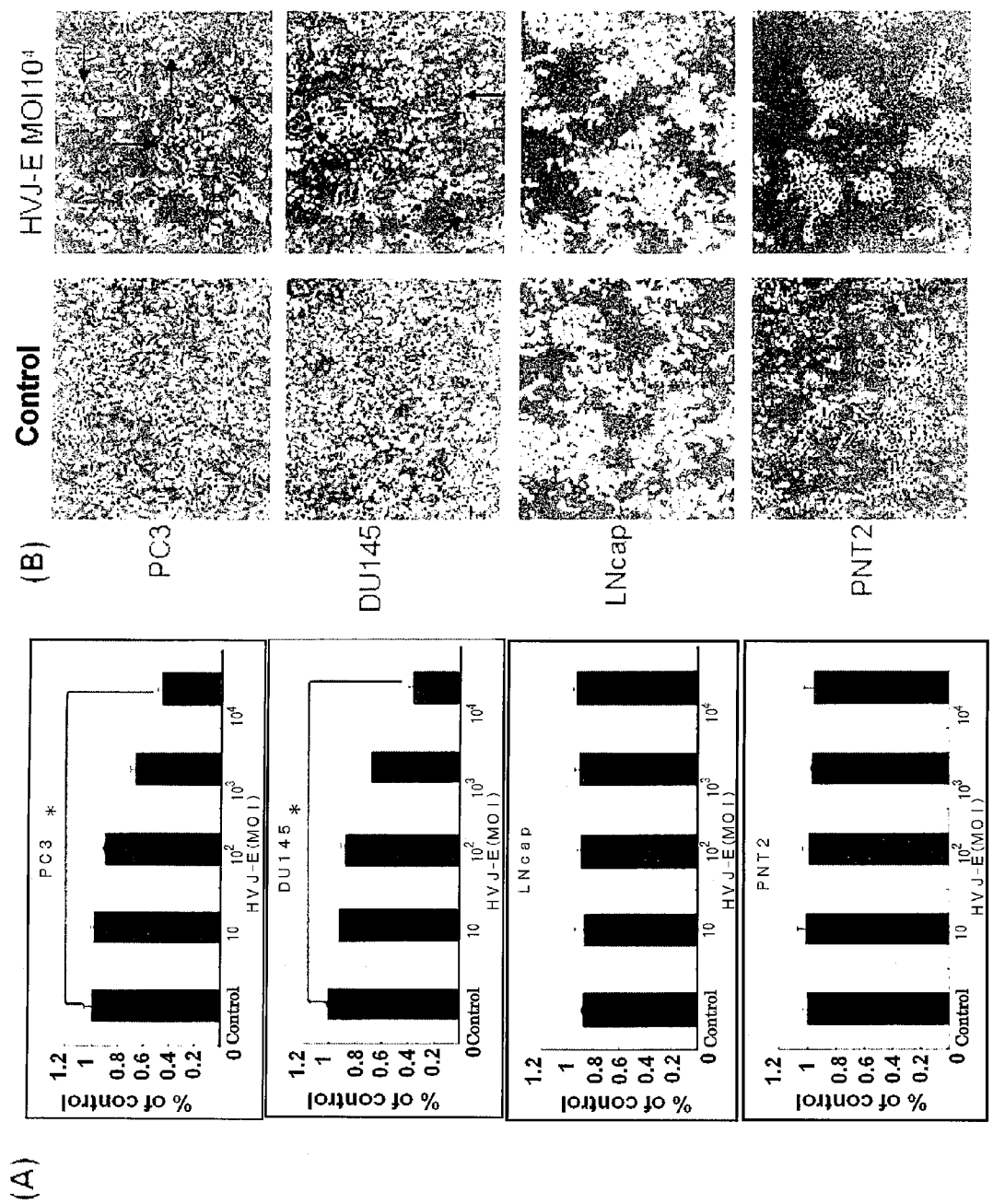
FIG. 1 presents data showing the ability of the Sendai viral envelope to kill prostatic cancer cells (non-hormone-refractory prostatic cancer cell LNCap, hormone-refractory prostatic cancer cells PC3 and DU145) or normal human prostatic epithelial cells (PNT2). (A) shows survival rates of prostatic cancer cells or normal human prostatic epithelial cells compared with controls (y-axis) versus the number of virions of the Sendai viral envelope (x-axis); (B) shows representative morphologies thereof (magnification rate ×40). Each arrow indicates a cell fused with the Sendai viral envelop.

The present invention is hereinafter described in detail.

The present invention provides a prostatic cancer therapeutic/prophylactic agent containing a viral envelope as an active ingredient.

As used herein, "a viral envelope" means a membraneous structure located on the outermost side of a virus. In the virus, the envelope normally covers the viral genome and capsid protein. The viral envelope is normally capable of carrying a variety of substances in the intima thereof, and possesses the activity of fusing with the cell membrane and transferring the substances contained in the intima into cells. For this reason, by enclosing in the intima of the viral envelope a desired substance [a gene (for example, DNA, RNA and the like), protein (or peptide), compound (anticancer agent, antibacterial agent, immunity promoter and the like)], and administering this to an individual, it is possible to deliver the desired substance into a variety of tissues and cells. Hence, viral envelopes can be used as vectors of a variety of substances. The viral envelope used in the present invention may have a substance intended to be introduced to a living organism or a cell, enclosed or not enclosed in the interior thereof. As shown in an Example below, the viral envelope itself has an effect to kill prostatic cancer cells, so that in a preferred embodiment, a substance intended to be introduced to a living organism or a cell is not substantially enclosed in the viral envelope.

The virus used to prepare the viral envelope of the present invention may be any virus having an envelope, whether a DNA virus or an RNA virus. The virus of the present invention may be a wild-type virus or a recombinant type virus.

Such viruses include, but are not limited to, Poxviridae, Herpesviridae, Hepadnaviridae, and Baculoviridae, which belong to DNA viruses, and Retroviridae, Togaviridae, Coronaviridae, Flaviviridae, Paramyxoviridae, Orthomyxoviridae, Bunyaviridae, Rhabdoviridae, Arenaviridae, and Filoviridae and the like, which belong to RNA viruses. In the present invention, of the aforementioned viruses, viruses belonging to Paramyxoviridae are preferably used.

Specific examples of preferred viruses include Sendai virus, retrovirus, adeno-associated virus, herpes virus, vaccinia virus, pox virus, influenza virus and the like; most preferably, Sendai virus is used.

Sendai viruses used in the present invention, for example, VR-105, VR-907 and the like, can be purchased from the American Type Culture Collection (ATCC; address: P.O. Box 1549, Manassas, Va. 20108 USA, TEL [1]-703-365-2700). http://www.atcc.org/ATCCAdvancedCatalogSearch/ProductDetails/tabid/452/Default.aspx?ATCCNum=VR-105&Template=animalVirology Viral envelopes are described in more detail in, for example, JP2001-286282A (WO 01/57204), JP2002-065278A, WO 03/014338 and the like, and can specifically be prepared in accordance with, for example, Example 8 of JP-A-2001-286282 and the like. Alternatively, the Sendai viral envelope can also be prepared by proliferating Sendai virus, and isolating and purifying the envelope from the virus recovered, according to methods described in Examples below herein.

The viral envelope used in the present invention may be an inactivated virus. An inactivated virus can be obtained by inactivation-treating a viral genome. Examples of inactivation treatment include UV treatment and alkylation treatment. This inactivation treatment of the viral genome causes the genomic DNA or RNA to become denatured or fragmented in the viral envelope. Specifically, the Sendai viral envelope can also be inactivated according to a method described in an Example below.

The viral envelope used in the present invention may be one that has been isolated and purified. "Isolated and purified" means that an operation for removing ingredients other than the desired product (viral genome, capsid protein and the like) has been performed.

Herein, "prostatic cancers" encompass cancers that have developed in the prostate and are localized to the prostate, cancers that have developed in the prostate and have infiltrated outside of the prostate, and metastatic/recurrent cancers derived from cancers that have developed in the prostate.

Because prostatic cancers grow androgen-dependently initially after onset, endocrine therapy (hormone therapy) wherein the amounts of androgens secreted in the body and the actions of androgens are suppressed by extirpation of androgen-secreting tissues (testis, adrenals and the like), administration of an antagonizing inhibitor of androgens and the like, is often effective. Examples of "androgens" include testosterone, dihydrotestosterone, dehydroepiandrosterone, androsterone, androstendione and the like. Herein, "endocrine therapy (hormone therapy)" refers to a therapeutic method for suppressing the proliferation of prostatic cancer cells by suppressing the secretion and functioning of androgens. Specific means of endocrine therapy (hormone therapy) include orchiectomy (castration surgery) and drug therapies; drug therapies include administration of LH-RH agonists, anti-male hormone agents (anti-androgen agents), or female hormone agents (estrogen agents) and the like. However, it is known that continuing this therapy reduces the androgen susceptibility of prostatic cancer cells, which in turn makes the cells capable of proliferating non-androgen-dependently. As a result, the efficacy of endocrine therapy (hormone therapy) for prostatic cancers weakens. The therapeutic/prophylactic agent of the present invention is particularly effective on prostatic cancers whose androgen susceptibility has been partially or completely reduced like this. "Androgen susceptibility" means a degree of promotion of the proliferation of prostatic cancer cells by androgen stimulation. "A complete reduction in androgen susceptibility" means that prostatic cancer growth is not promoted at all by androgen stimulation. "A partial reduction in androgen susceptibility" means that although prostatic cancer growth is promoted due to androgen stimulation, the degree is lower than that obtained initially after the onset of the prostatic cancer. Also, the therapeutic/prophylactic agent of the present invention is effective particularly on hormone-refractory prostatic cancers. "Hormone-refractory" refers to a state of prostatic cancer wherein endocrine therapy (or hormone therapy) has become partially or completely ineffective due to a reduction in the androgen susceptibility, also encompassing androgen-refractory prostatic cancers. "Endocrine therapy is partially ineffective" refers to a state wherein prostatic cancer growth is partially suppressed, but the growth is not completely terminated by endocrine therapy. "Endocrine therapy is completely ineffective" refers to a state wherein prostatic cancer growth is not suppressed at all by endocrine therapy.

Although it remains unknown why viral envelopes are effective particularly on prostatic cancers wherein the androgen susceptibility has been partially or completely reduced and hormone-refractory prostatic cancers, one reason seems to be that viral envelops are capable of fusing specifically with prostatic cancer cells possessing these characteristics.

Herein, "treatment" refers to delaying the progression of the target cancer, or shrinking or disappearing the cancer tissue. Hence, not only killing cancer cells completely or partially, but also completely or partially suppressing or delaying the proliferation of cancer cells are encompassed. "Prevention" can also encompass suppressing the onset of a prostatic cancer in advance by administeration to a patient at a risk of contracting a prostatic cancer, and preventing the recurrence/metastasis of a cancer by administeration to a patient after prostatic cancer treatment.

While the mechanism by which the viral envelope used in the present invention prevents or treats prostatic cancers remains to be clarified in full, it is thought that combining the actions of viral envelopes described below, the viral envelope exhibits its excellent therapeutic/prophylactic effect on prostatic cancers.

(Induction of Apoptosis)

Viral envelopes are capable of acting directly on prostatic cancer cells to induce apoptosis. Accordingly, the therapeutic/prophylactic agent of the present invention is useful as an inducer of apoptosis to prostatic cancer cells. Apoptosis refers to genetically controlled cell death, as defined by two biochemical changes: cell morphological changes and DNA fragmentation in nucleosome units.

(Induction of Production of Interferon α or β)

Viral envelopes induce the production of the cytokines interferons α and/or β to prostatic cancer cells. Interferons α and β are known to possess a potent antitumor effect, activate NK cells, act directly on tumor cells, and suppress their proliferation.

(Activation of NK Cells)

As shown in an Example below, in a mouse lacking NK cells due to an anti-acialo GM1 antibody treatment, the therapeutic effect of viral envelopes on prostatic cancers has weakened. Therefore, at least some of the antitumor effects of viral envelopes are thought to have been achieved as the viral envelope activates NK cells (acialo GM1-positive cells) directly or indirectly.

(Activation of Cytotoxic T Cells)

Viral envelopes activate cytotoxic T cells (CTL). Therefore, viral envelopes are capable of exhibiting not only a direct cytotoxic effect, but also an antitumor effect via antitumor immunity.

The therapeutic/prophylactic agent of the present invention can be administered via an optionally chosen route. However, viral envelopes are capable of acting directly on prostatic cancer cells to induce the apoptosis thereof, as stated above; therefore, an even higher therapeutic effect can be obtained by administering the therapeutic/prophylactic agent of the present invention in a way such that the viral envelope is allowed to come in contact with prostatic cancer cells as efficiently as possible. From this viewpoint, it is desirable that the therapeutic/prophylactic agent of the present invention be subcutaneously administered or administered directly to prostatic cancer tissue and/or the vicinity thereof. Here, "direct administration" may be performed, as far as the drug administered is delivered to the cancer tissue; direct administration is possible by injection, coating, spraying, or targeting in combination with a drug delivery system, and the like. Hence, direct administration allows the drug to act topically on the cancer tissue being treated. To maximize the therapeutic/prophylactic effect of the viral envelope, the therapeutic/prophylactic agent of the present invention is preferably injected directly into prostatic cancer tissue.

In an embodiment, the prostatic cancer therapeutic/prophylactic agent of the present invention contains a viral envelope having substantially nothing enclosed therein artificially as an active ingredient. In some cases, it is also possible to formulate the agent as a single preparation along with one or more other kinds of ingredients that are effective in cancer treatment/prevention, but these active ingredients are not artificially enclosed in the envelope.

Whatever the dosage form thereof is, the cancer therapeutic/prophylactic agent in the present invention includes pharmaceutical compositions such as injections, ointments, and sprays. Preferably, the dosage form is an injection. Furthermore, currently, targeting techniques for delivering a substance (a drug and the like) preferentially or specifically to a variety of cancer tissues are being developed or are expected to be developed in the future. The therapeutic/prophylactic agent of the present invention can also be used along with these targeting techniques and formulated in a way such that it is targeted to cancer tissue.

Those skilled in the art are able to formulate the cancer therapeutic/prophylactic agent of the present invention as a pharmaceutical composition according to the method of administration thereof.

As required in pharmaceutical making, an appropriate pharmaceutically acceptable carrier, for example, an excipient, a binder, a lubricant, a solvent, a disintegrant, a solubilizer, a suspending agent, an emulsifier, an isotonizing agent, a stabilizer, a soothing agent, an antiseptic, an antioxidant, a corrective, a coloring agent and the like are formulated.

As the excipient, organic excipients such as saccharides such as lactose, glucose, and D-mannitol, starches, and celluloses such as crystalline cellulose, inorganic excipients such as calcium carbonate and kaolin and the like can be mentioned; as the binder, gelatinized starch, gelatin, gum arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, polyvinyl alcohol and the like can be mentioned; as the lubricant, stearic acid, fatty acid salts such as stearates, talc, silicates and the like can be mentioned; as the solvent, purified water, physiological saline and the like can be mentioned; as the disintegrant, low-substitution hydroxypropylcellulose, chemically modified cellulose and starches and the like can be mentioned; as the solubilizer, polyethylene glycol, propylene glycol, trehalose, benzyl benzoate, ethanol, sodium carbonate, sodium citrate, sodium salicylate, sodium acetate and the like can be mentioned; as the suspending agent or emulsifier, sodium lauryl sulfate, gum arabic, gelatin, lecithin, monostearic glycerol, polyvinyl alcohol, polyvinylpyrrolidone, celluloses such as carboxymethylcellulose sodium, polysorbates, polyoxyethylene hardened castor oil and the like can be mentioned; as the isotonizing agent, sodium chloride, potassium chloride, saccharides, glycerin, urea and the like can be mentioned; as the stabilizer, polyethylene glycol, sodium dextran sulfate, other amino acids and the like can be mentioned; as the soothing agent, glucose, calcium gluconate, procaine hydrochloride and the like can be mentioned; as the antiseptic, paraoxybenzoates, chlorobutanol, benzyl alcohol, phenethyl alcohol, dehydroacetic acid, sorbic acid and the like can be mentioned; as the antioxidant, sulfites, ascorbic acid and the like can be mentioned; as the corrective, sweeteners, flavoring agents and the like in common use in the pharmaceutical area can be mentioned; as the coloring agent, coloring agents in common use in the pharmaceutical area can be mentioned.

Regarding the dose of the cancer therapeutic/prophylactic agent of the present invention, the agent can be administered in a therapeutically/prophylactically effective amount. A specific dose can be determined according to the patient's condition by a general physician or a competent person in the clinical setting. Varying depending on the recipient patient's age, body weight, and pathologic condition, the method of administration and the like, the agent is normally administered in an amount of 100 to 40,000 HAU, preferably 500 to 20,000 HAU, more preferably 1,000 to 10,000 HAU, particularly preferably 5,000 HAU or less, for an adult, based on the Sendai viral envelope.

Administration frequency can also be determined according to the patient's condition by a general physician or a competent person in the clinical setting. Generally, multiple-dose administration is preferred, but this is not to be construed as limiting.

For example, a method of administration wherein an injection is administered directly to cancer tissue by 3 times of direct injection at 3-day intervals, and the like are feasible.

The cancer therapeutic/prophylactic agent of the present invention can be used alone in a therapeutically/prophylactically effective amount. Alternatively, after a treatment is performed with the prostatic cancer therapeutic agent of the present invention, or during continued administration, the cancer can be removed partially or completely by surgical treatment. Furthermore, the prostatic cancer therapeutic agent of the present invention can also be administered in combination with another drug, for example, a chemotherapy agent. In this case, the prostatic cancer therapeutic drug of the present invention and the other drug may be administered simultaneously or sequentially in an optionally chosen order.

Furthermore, the prostatic cancer therapeutic/prophylactic agent of the present invention can also be used in combination with any other cancer therapeutic method. Other cancer therapeutic methods include, but are not limited to, for example, surgical resection, endocrine therapy, radiotherapy, chemotherapy, immunotherapy and the like. Before or after, or simultaneously with, these other therapeutic methods, the therapeutic/prophylactic agent of the present invention can be administered. Hence, the therapeutic/prophylactic agent of the present invention can be administered to i) prostatic cancer patients who have ever been on another therapeutic method, ii) prostatic cancer patients who are on treatment by another therapeutic method, or iii) prostatic cancer patients who are scheduled to receive another therapeutic method. Here, "endocrine therapy" is as described above. Also, "radiotherapy" refers to irradiating radiation for the purpose of controlling a tumor by the electrolytic dissociation action of the radiation. As used herein, "chemotherapy" refers to performing a cancer treatment using an anticancer agent. As used herein, "immunotherapy" indicates a therapeutic method for treating a cancer, or delaying its progression, by improving the immune function in the patient's body. Generally, vaccine therapy, cellular adoptive immunotherapy, cytokine therapy, BRM therapy and the like can be mentioned. As stated above, the viral envelope of the present invention is effective particularly on prostatic cancers whose androgen susceptibility has been partially or completely reduced, and hormone-refractory prostatic cancers. Therefore, by using the therapeutic/prophylactic agent of the present invention in combination with endocrine therapy, both non-hormone-refractory prostatic cancer cells and hormone-refractory prostatic cancer cells can be removed. In a preferred embodiment, the therapeutic/prophylactic agent of the present invention is administered to a prostatic cancer patient having a history of receiving endocrine therapy. The prostatic cancer patient having a history of receiving endocrine therapy sometimes bears a prostatic cancer whose androgen susceptibility has been partially or completely reduced or a hormone-refractory prostatic cancer as a result of endocrine therapy; in such cases, the therapeutic/prophylactic agent of the present invention is particularly advantageous.

The prostatic cancer therapeutic agent of the present invention suppresses the increase in the volume of cancer tissue. Specifically, the prostatic cancer therapeutic agent of the present invention is capable of reducing the increase in the volume by 30% or more, preferably 50% or more, more preferably 60% or more, particularly preferably 70% or more, compared with prostatic cancer tissue undergoing no treatment. As described in an Example below, by 3 times of direct administeration to cancer tissue by injection at 3-day intervals, the increase in the volume of the cancer tissue after administration can be suppressed by 90% or more, or 95% or more, over 30 days or more after final administration. This dramatic effect of the Sendai viral envelope was found for the first time by the present invention. The prostatic cancer therapeutic agent of the present invention is characterized by the presence of an active ingredient consisting substantially of the Sendai viral envelope. Therefore, adverse reactions (nausea, hair loss and the like) due to conventional chemotherapeutic agents are absent.

The mechanism behind the antitumor effect of the inactivated viral envelope of the present invention is estimated as described below, but this is not to be construed as limiting. Receptors of the Sendai viral envelope on the cell membrane are a class of gangliosides; GD1a, in particular, is a major receptor. This ganglioside is nearly absent in normal prostatic epithelium, but is intensively expressed in hormone-refractory prostatic cancers. Therefore, when the Sendai viral envelope is contacted with hormone-refractory prostatic cancer cells, it efficiently causes cell fusion to inhibit cell proliferation. Meanwhile, virus-derived double-stranded RNA binds to the intracellular viral genome receptor RIG-I, the resulting signal transduction stimulates cancer cells to secrete interferon-$\alpha$ and $\beta$, and the cancer cells activate caspase 3 and 8 to cause apoptosis with the interferons secreted by themselves. However, normal prostate cells are not influenced, with no interferons secreted by the action of the Sendai viral envelope. Furthermore, the Sendai viral envelope also promotes the enhancement of the expression of RIG-I, and enhances this cancer cell-specific apoptosis induction effect. In a mouse tumor model, in addition to this effect, as found by the present inventors in a mouse model of renal cancer, it was found that NK cells capable of attacking tumors as well were also activated, thus further enhancing the antitumor effect. Although verification cannot be achieved in a mouse model of human prostatic cancer, it is anticipated that T cells that are cytotoxic to tumors will also be activated, as we have already reported on an experiment of treatment of colorectal cancer; in addition to the direct tumor killing effect, it is expected that administration of the Sendai viral envelope to localized cancer foci suppresses not only primary foci, but also remote metastases, and prevents recurrences, even in treatment-refractory cancers, as a result of activation of host immunity to tumors.

Furthermore, the Sendai viral envelope of the present invention alone exhibits a tumor regression effect on melanoma as well. Accordingly, the present invention provides a melanoma therapeutic/prophylactic agent containing the Sendai viral envelope as the only active ingredient. As mentioned with regard to melanoma, "treatment" or "prevention" has the same definition as the aforementioned "treatment" or "prevention" with regard to prostatic cancers.

Containing the Sendai viral envelope as the only active ingredient refers to the fact that any one or more kinds of ingredients having an antitumor effect are not enclosed in the envelope, or not contained in the therapeutic/prophylactic agent. Also, herein, "melanoma" also encompasses cancers that have developed in the skin, orbital tissue, oral mucosal epithelium and the like, and are localized in these onset sites, cancers that have developed in the skin, orbital tissue, oral mucosal epithelium and the like, and have infiltrated outside of these onset sites, and metastatic/recurrent cancers derived from cancers that have developed in the skin, orbital tissue, oral mucosal epithelium and the like.

Whatever the dosage form thereof is, the melanoma therapeutic/prophylactic agent of the present invention includes pharmaceutical compositions such as injections, ointments, and sprays. Preferably, the dosage form is an injection. Furthermore, currently, targeting techniques for delivering a substance (a drug and the like) preferentially or specifically to a variety of cancer tissues are being developed or are expected to be developed in the future. The melanoma therapeutic/prophylactic agent of the present invention can also be used along with these targeting techniques and formulated in a way such that it is targeted to cancer tissue. Those skilled in the art are able to formulate the melanoma therapeutic/prophylactic agent of the present invention as a pharmaceutical composition according to the method of administration thereof; as required for pharmaceutical making, pharmaceutically acceptable carriers and the like used in the aforementioned prostatic cancer therapeutic/prophylactic agent can be used as appropriate.

Regarding the dose of the melanoma therapeutic/prophylactic agent of the present invention, the agent can be administered in a therapeutically/prophylactically effective amount. A specific dose can be determined according to the patient's condition by a general physician or a competent person in the clinical setting. Varying depending on the recipient patient's age, body weight, and pathologic condition, the method of administration and the like, the agent is normally administered in an amount of 10 to 1,0000 HAU, preferably 40 to 400 HAU, for an adult, based on the Sendai viral envelope.

Administration frequency can also be determined according to the patient's condition by a general physician or a competent person in the clinical setting. Generally, multiple-dose administration is preferred, but this is not to be construed as limiting.

For example, a method of administration wherein an injection is administered directly to cancer tissue by 1 to 10, preferably 3 to 6, times of direct injection, and the like are feasible. The time interval of administration can also be determined according to the patient's condition, and the injection can be administered at intervals of, for example, 2 or 3 days.

The present invention is hereinafter described in detail by means of the following Examples, to which, however, the invention is not limited in any way.

EXAMPLES

Example 1

Preparation of Inactivated Sendai Viral Envelope Using Surfactant (1: Proliferation of Sendai Virus)

Although Sendai viruses proliferated by inoculating a seed virus to a fertilized chicken egg are generally useful, those proliferated by utilizing a system for persistent viral infection of cultured cells or cultured tissues of monkeys, humans and the like (a hydrolase such as trypsin added to culture broth) and those proliferated by infecting cultured cells with a cloned viral genome to cause persistent infection can all be utilized.

In this Example, proliferation of Sendai virus was performed as described below. A seed virus of Sendai virus was proliferated using an SPF (Specific pathogen free) fertilized egg, and separated and purified; the resulting Sendai virus (Z strain) was dispensed to a cell preservation tube, and preserved and prepared in liquid nitrogen with the addition of 10% DMSO.

Chicken eggs just after fertilization were received, placed in an incubator (SHOWA-FURANKI P-03 model; about 300 eggs accommodated), and reared under conditions of 36.5° C. and a humidity of 40% or more for 10 to 14 days. In a dark room, using an egg candler (electric bulb light emitted through an window of about 1.5 cm diameter), embryo survival and the air chamber and the chorioallantoic membrane were checked, and the virus injection site was marked with a pencil about 5 mm above the chorioallantoic membrane (a site except a thick blood vessel chosen). The seed virus (as taken out from liquid nitrogen) was diluted 500 fold with polypeptone solution (1% polypeptone and 0.2% NaCl blended, adjusted to pH 7.2 with 1M NaOH, autoclaved, and preserved at 4° C.), and this was allowed to stand at 4° C. The eggs were disinfected with Isodine and alcohol; a small hole was made in the virus injection site using an awl, and 0.1 ml of the diluted seed virus was injected into the chorioallantoic cavity using a 1 ml syringe equipped with a 26-gauge needle. Melted paraffin (melting point 50 to 52° C.) was placed on the hole using a Pasteur pipette to cover the hole. The eggs were placed in an incubator, and reared under conditions of 36.5° C. and a humidity of 40% or more for 3 days. Next, the inoculated eggs were allowed to stand at 4° C. overnight. The following day, the air chamber portion of each egg was cleaved using tweezers, a 10 ml syringe equipped with an 18-gauge needle was placed in the chorioallantoic membrane, and the chorioallantoic fluid was collected in a sterile bottle by aspiration and preserved at 4° C.

(2: Purification of Sendai Virus)

Sendai virus can be purified using centrifugation-based methods of purification, methods of purification with a column, or other methods of purification known per se in the field.

(2.1: Method of Purification by Centrifugation)

Briefly, a proliferated virus liquid was recovered by low-speed centrifugation, and tissue/cell fragments in the culture broth and chorioallantoic fluid were removed. The supernatant was purified by high-speed centrifugation (27,500×g, 30 minutes) and ultracentrifugation (62,800×g, 90 minutes) on a sucrose density gradient (30 to 60% w/v). Cautions should be exerted to handle the virus as gently as possible during the purification, and preserve it at 4° C.

In this Example, specifically, Sendai virus was purified by the method described below.

About 100 ml of a chorioallantoic fluid containing Sendai virus (chorioallantoic fluid of a chicken egg containing Sendai virus gathered and preserved at 4° C.) was placed in two 50 ml centrifugal tubes using a wide-mouthed Komagome pipette (see Saeki, Y., and Kaneda, Y: Protein modified liposomes (HVJ-liposomes) for the delivery of genes, oligonucleotides and proteins. Cell Biology; A laboratory handbook (2nd edition), edited by J. E. Celis (Academic Press Inc., San Diego), vol. 4, 127-135, 1998), and centrifuged at 3,000 rpm for 10 minutes at 4° C. (brake set off), and egg tissue fragments were removed.

After the centrifugation, the supernatant was dispensed to four 35 ml centrifugal tubes (for high-speed centrifugation), and centrifuged at 27,000×g using an angle rotor for 30 minutes (accelerator and brake set on). The supernatant was removed, BSS (10 mM Tris-HCl (pH 7.5), 137 mM NaCl, 5.4 mM KCl; autoclaved and preserved at 4° C.) (PBS acceptable in place of BSS) was added to the precipitate at about 5 ml per tube, and the precipitate was allowed to stand as it was at 4° C. overnight. The precipitate was loosened by gentle pipetting using a wide-mouthed Komagome pipette, gathered in a single tube, and centrifuged at 27,000×g using an angle rotor for 30 minutes in the same way as the above. The supernatant was removed, about 10 ml of BSS was added to the precipitate, and the precipitate was allowed to stand at 4° C. overnight in the same manner as the above. The precipitate was loosened by gentle pipetting using a wide-mouthed Komagome pipette, centrifuged using a low-speed centrifuge at 3,000 rpm for 10 minutes at 4° C. (brake set off), and the tissue fragments and virus agglutination masses remaining unremoved were removed. The supernatant was placed in a new sterile tube, and this was preserved as the purified virus at 4° C.

0.9 ml of BSS was added to 0.1 ml of this virus liquid, the absorbance at 540 nm was measured using a spectrophotometer, and the virus titer was converted to an erythrocyte agglutination activity (HAU). An absorbance value of 1 at 540 nm nearly equaled 15,000 HAU. Herein, HAU (Hemagglutinating unit) is a unit of the activity for agglutinating erythrocytes, 1 HAU of HVJ-E refers to the least unit that causes agglutination when the HVJ-E is mixed with chicken erythrocytes. HAU is thought to be nearly proportional to fusion activity. Erythrocyte agglutination activity may be measured by actually using a chicken erythrocyte liquid (0.5%) (see Dobutsu Saibou Riyou Jitsuyouka Manual, REALIZE INC. (Uchida, Oishi, Furusawa editors) P259 to 268, 1984).

Furthermore, purification of Sendai virus using a sucrose density gradient can also be performed as required. Specifically, a virus suspension is mounted on a centrifugal tube with 60% and 30% sucrose solutions (autoclaved) overlain each other therein, and subjected to density gradient centrifugation at 62,800×g for 120 minutes. After the centrifugation, the band seen on the 60% sucrose solution layer is recovered. The recovered virus suspension is dialyzed against BSS or PBS as the external fluid at 4° C. overnight to remove the sucrose. When the virus suspension is not to be used soon, glycerol (autoclaved) and 0.5M EDTA liquid (autoclaved) are added to the virus suspension to obtain final concentrations of 10% and 2 to 10 mM, respectively, and the virus suspension is gently frozen at −80° C., and finally preserved in liquid nitrogen (freezing preservation also possible using 10 mM DMSO in place of glycerol and 0.5M EDTA liquid).

(2.2: Methods of Purification Using Column and Ultrafiltration)

In place of the method of purification by centrifugation, purification of Sendai virus using a column is applicable to the present invention.

Briefly, Sendai virus was purified using concentration by ultrafiltration through a filter having a molecular weight cut-off value of 50,000 (about 10 fold) and elution by ion exchange chromatography (0.3M to 1M NaCl).

Specifically, in this Example, Sendai virus was purified through a column using the method described below.

After collection, chorioallantoic fluid was filtered through 80 μm to 10 μm membrane filters. 0.006 to 0.008% BPL (final concentration) was added to the chorioallantoic fluid (4° C., 1 hour) to inactivate the Sendai virus. By incubating the chorioallantoic fluid at 37° C. for 2 hours, the BPL was inactivated.

The chorioallantoic fluid was concentrated about 10 fold by tangential flow ultrafiltration using 500KMWCO (A/G Technology, Needham, Mass.). Used as the buffer solution was 50 mM NaCl, 1 mM $MgCl_2$, 2% mannitol, 20 mM Tris (pH 7.5). HAU assay yielded favorable results with a Sendai virus recovery rate of nearly 100%.

Sendai virus was purified by a column chromatography method (buffer solution: 20 mM Tris-HCl (pH 7.5), 0.2 to 1M NaCl) using QSepharose FF (Amersham Pharmacia Biotech K.K., Tokyo). The recovery rate was 40 to 50%, the purity being more than 99%.

The Sendai virus fraction was concentrated by tangential flow ultrafiltration using 500KMWCO (A/G Technology).

(3: Inactivation of Sendai Virus)

Inactivation of Sendai virus was performed by ultraviolet irradiation as described below.

(3.1: Method of Ultraviolet Irradiation)

1 ml of the Sendai virus suspension was placed in a Petri dish 30 mm across, and exposed to 99 or 198 millijoules/$cm^2$. The inactivated virus does not have a replication potential, but retains the potential for fusing with viruses.

Example 2

Antitumor Effect of Sendai Viral Envelope In Vitro

PC3 cells, DU145 cells and LNCap cells were purchased from the American Type Culture Collection (Rockville, Md.). The DU145 cells were cultured in the presence of 10% fetal bovine serum (FBS), 100 U/mL penicillin, and 100 μg/mL streptomycin in RPMI1640 medium (Nakarai Tesque, Kyoto, Japan). The PC3 cells were cultured in the presence of 10% FBS, 100 U/mL penicillin, and 100 μg/mL streptomycin in Dulbecco's modified Eagle F12 medium. All cell cultures were performed under humidified conditions of 37° C. and 5% $CO_2$.

PC3 cells and DU145 cells, which are hormone-refractory prostatic cancer cells, and a non-hormone-refractory prostatic cancer cell line of LNCap cells, or normal human prostatic epithelial cells (PNT2) were seeded to respective 96-well plates at a density of 1×10⁴ cells/well; 24 hours later, the cells were reacted with the Sendai viral envelope [multiplicity of infection (MOI): 10 to $10^4$]. The cells were further cultured for 24 hours, and cell survival rates were examined by MTS assay using Celltiter 96® Aqueous One Solution Cell Proliferation Assay (Promega, USA). The survival rates are expressed as ratios to respective Sendai viral envelope no-treatment groups (controls); a graph representation is shown in FIG. 1(A). In all types of hormone-refractory prostatic cancer cells, the viable cell count decreased Sendai viral envelope concentration-dependently; in the cells treated with MOI $10^4$ Sendai viral envelope, the viable cell count decreased to 46% for PC3 cells, and to 35% for DU145 cells, compared with the control. Meanwhile, within the said range of concentrations, the Sendai viral envelope did not influence the survival rates of the non-hormone-refractory prostatic cancer cells and normal prostatic epithelial cells. Microscopic images of a control and MOI $10^4$ Sendai viral envelope treatment of each cell line are shown in FIG. 1(B) (magnification rate ×40).

In the non-hormone-refractory prostatic cancer cells and normal prostatic epithelial cells, cell death due to the Sendai viral envelope was not noted; the Sendai viral envelope induced cell death selectively to the hormone-refractory (prostate) cancer cells. This demonstrated a selective antitumor effect of the Sendai viral envelope on the hormone-refractory prostatic cancer cells.

Example 3

Combined Cell Adhesion and Cell Membrane Fusion Effect of Sendai Viral Envelope In Vitro Hormone-refractory prostatic cancer cell line PC3 cells and DU145 cells, non-hormone-refractory prostatic cancer cells LNCap and normal human prostatic epithelial cells (PNT2) were seeded onto a polyethylenimine-coated cover glass placed in each 6-well plate at a density of 2×10⁵ cells/well. The following day, the cells were reacted with PKH26-labeled Sendai viral envelope (MOI $10^4$) at 37° C. for 60 minutes, after which the cells were twice washed with PBS, and fixed by 4% paraformaldehyde treatment (15 minutes, 4° C.). After the cell nucleus was counter-stained with DAPI, the cells were examined using a confocal microscope (magnification rate ×200).

Figure 2:
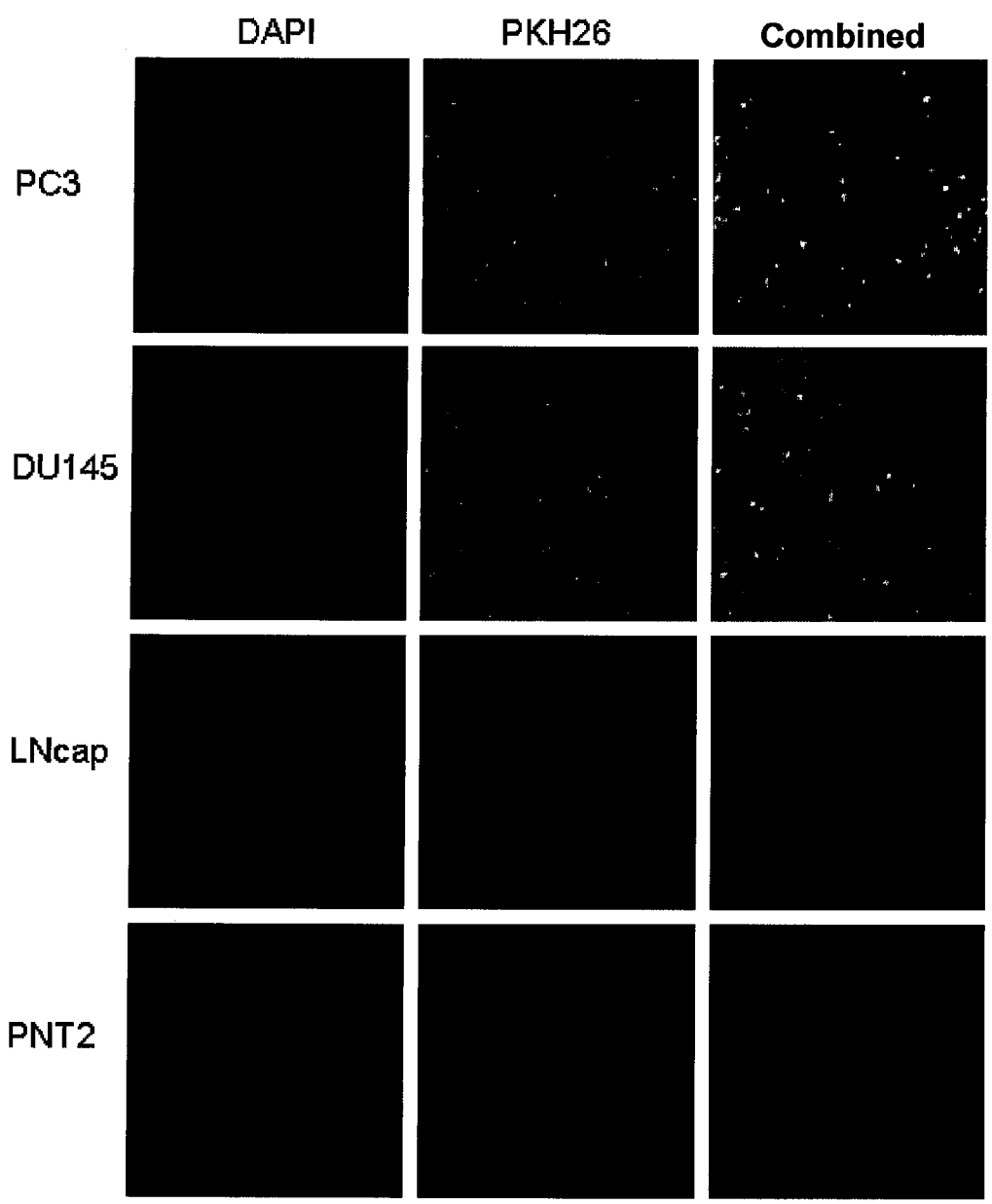
FIG. 2 presents data showing the ability of the Sendai viral envelope to adhere to hormone-refractory prostatic cancer cells (PC3, DU145), non-hormone-refractory prostatic cancer cells (LNCap cells) or normal human prostatic epithelial cells (PNT2). The PKH26-labeled Sendai viral envelope was administered to the hormone-refractory prostatic cancer cells, non-hormone-refractory prostatic cancer cells or human normal prostatic epithelial cells, and whether cell fusion would occur was examined (confocal magnification rate ×200). DAPI staining indicates a cell nucleus.

These findings demonstrated that the Sendai viral envelope exhibits an adhesion potential and membrane fusion potential for hormone-refractory prostatic cancer cells (FIG. 2).

Example 4

TUNEL Assay In Vitro

Figure 3:
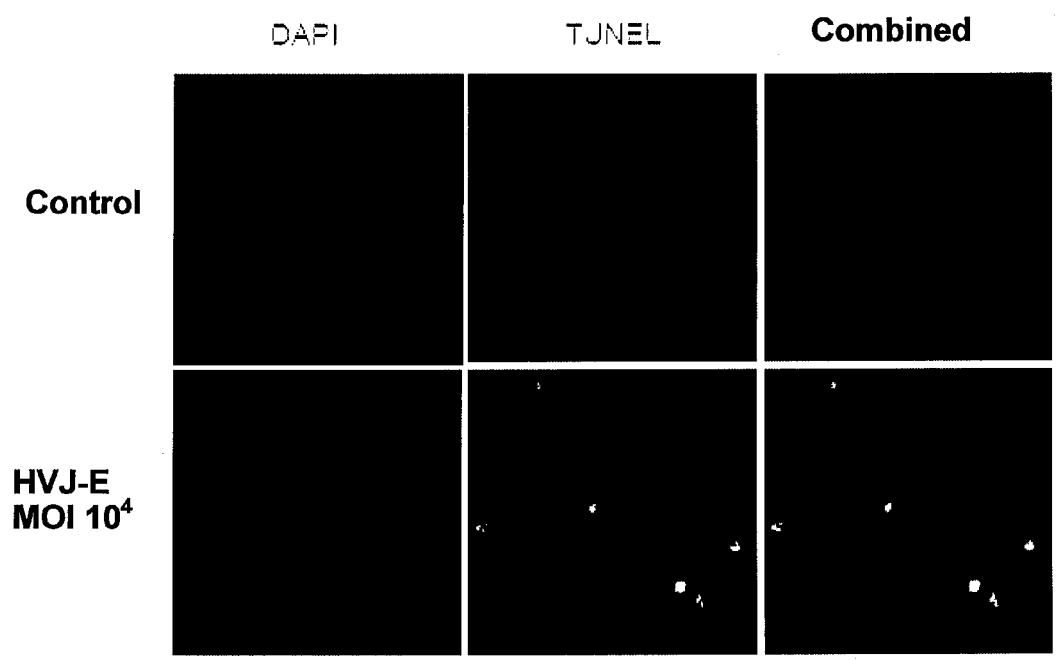
FIG. 3 presents data showing the ability of the Sendai viral envelope to induce apoptosis to hormone-refractory prostatic cancer cells (PC3). Shown are TUNEL-stained images of prostatic cancer cells after being treated with the Sendai viral envelope (MOI $10^4$), or as they were not treated (control) (confocal magnification rate ×200). DAPI staining indicates a cell nucleus.

PC3 cells were seeded onto a polyethylenimine-coated cover glass placed in a 6-well plate at a density of 1×10⁵ cells/well. The following day, the cells were reacted with the Sendai viral envelope (MOI $10^4$) and further cultured for 24 hours, after which the cells were twice washed with PBS and fixed by 4% paraformaldehyde treatment (15 minutes, 4° C.). Using an Apoptosis Detection Kit (TAKARA bio.), according to the procedures given in the instruction manual, apoptosis cells were detected by the terminal deoxynucleotide transferase (TdT)-mediated dUTP nick-end labeling (TUNEL) staining. Results of confocal microscopic examination (magnification rate ×200) are shown in FIG. 3. These findings demonstrated an increase in TUNEL-positive cells in the Sendai viral envelope administration group.

Example 5

Cell Death Inducing Effect of Sendai Viral Envelope In Vitro

Figure 4:
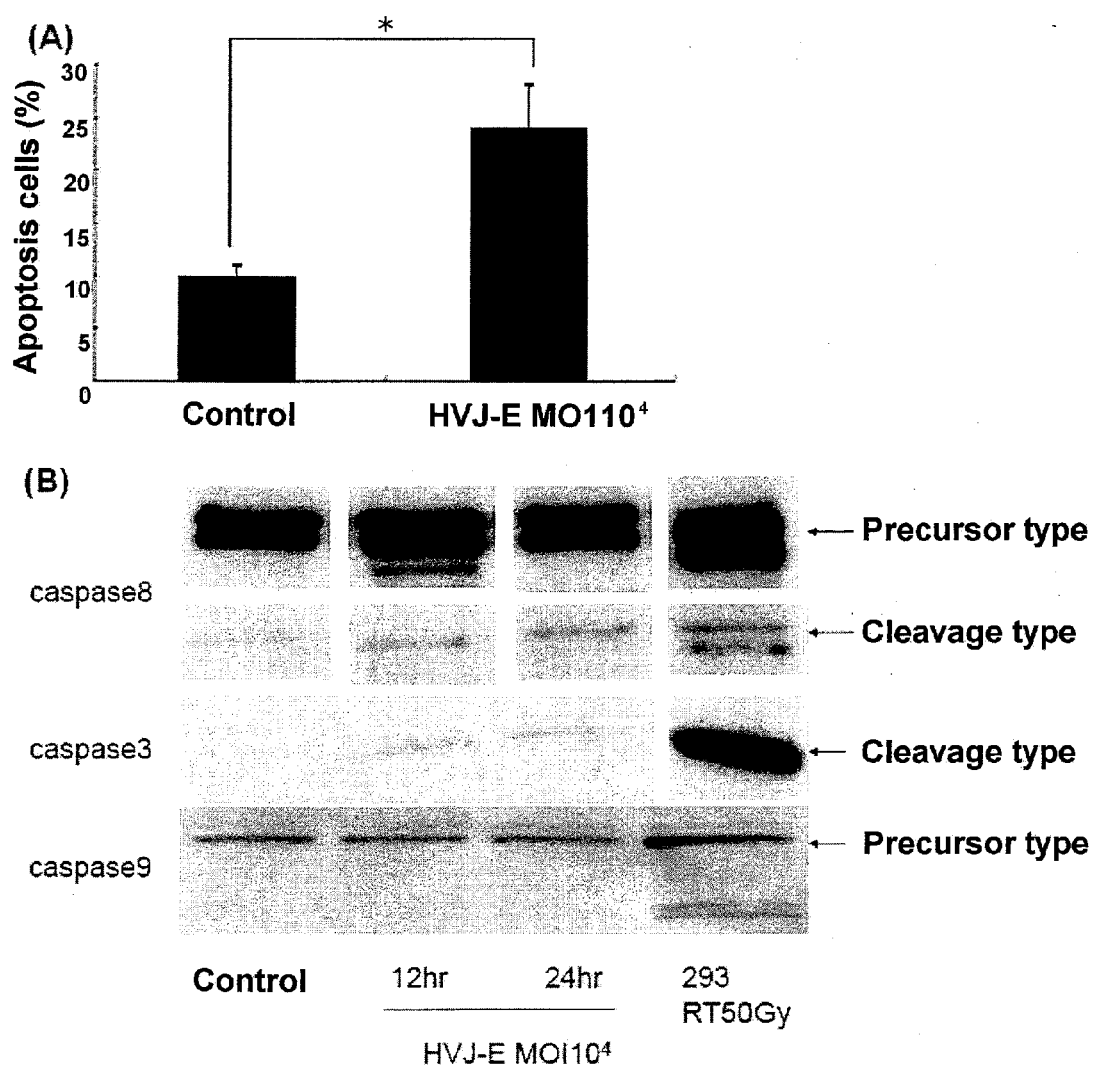
FIG. 4 presents data showing the potential of the Sendai viral envelope for inducing apoptosis to hormone-refractory prostatic cancer cells PC3. (A) compares annexin V-positive hormone-refractory prostatic cancer cells between a Sendai viral envelope treatment group and a no-treatment (control) group. (B) shows the expression of Caspase proteins in tumor cells at 12 and 24 hours after treatment with the Sendai viral envelope.

Using the Annexin V-FITC Apoptosis Detection Kit (BD Bioscience, CA, USA), differences in the ratio of apoptosis cells after Sendai viral envelope treatment were examined. PC3 cells were seeded to a 6-well plate at a density of 1×10⁵ cells/well; 24 hours later, the cells were reacted with the Sendai viral envelope (MOI $10^4$). The cells were further cultured for 24 hours, twice washed with PBS, re-suspended in a staining solution containing annexin V (5 μl) and propidium iodide (PI) (2 μl), and treated at room temperature in the dark for 15 minutes. The annexin V and propidium iodide had been purchased from BD PharMingen (San Diego, Calif.). The cells were analyzed using a FACScan flow cytometer (Becton Dickinson) with Cell Quest software. The results are shown in FIG. 4(A). In the group of cells treated with MOI $10^4$ of the Sendai viral envelope, compared with the control group not treated with the Sendai viral envelope, a more than 2-times increase in annexin V-positive cells was noted. Next, PC3 cells were seeded to a 6-well plate at a density of 1×10⁵ cells/well; 24 hours later, the cells were reacted with the Sendai viral envelope (MOI $10^4$). The cells were further cultured for 12 or 24 hours and twice washed with PBS, after which the cells were recovered and lysed with a lysis buffer. After an equal amount of a sample buffer was added thereto, the cell lysate was boiled for 10 minutes. For each sample, 10 μg of the protein was applied to 4-20% sodium dodecyl sulfate polyacrylamide gel, and analyzed by electrophoresis. After migration, the sample was transferred to a polyvinylidene fluoride membrane; the membrane was blocked with 5% skimmed milk and treated with a reaction mixture of 0.1% primary antibody and 5% skimmed milk at 4° C. overnight. Thereafter, the membrane was washed and reacted with an HRP-labeled anti-caspase 3 antibody (PC-020: TREVIGEN, MD, USA), anti-caspase 8 antibody (H-134: Santa Cruz, Calif., USA), and anti-caspase 9 antibody (H-83: Santa Cruz, Calif., USA) at room temperature for about 1 hour. Detection by chemiluminescence was performed per the protocol described in the ECL user's guide (Amersham). The results are shown in FIG. 4(B). In the cells treated with MOI $10^4$ of the Sendai viral envelope, increases in the expression of caspase 3 and 8 were noted compared with the control. Used as the positive control group was a sample exposed to radiation (RT50Gy). These findings demonstrated that the Sendai viral envelope exhibits a potential for inducing apoptosis to hormone-refractory prostatic cancer cells.

Example 6

IFN α and β Expression Inducing Effect of Sendai Viral Envelope In Vitro

Figure 5:
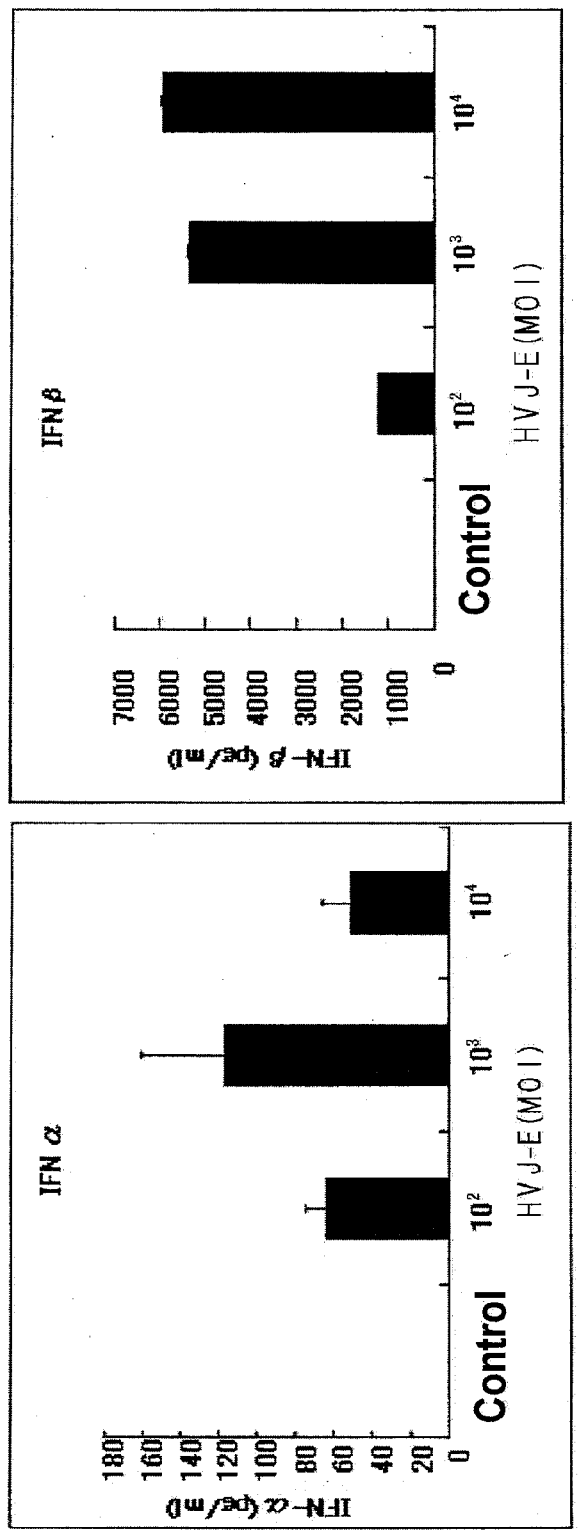
FIG. 5 presents data showing the potential of the Sendai viral envelope for inducing type I interferons to hormone-refractory prostatic cancer cells PC3.
Figure 5:
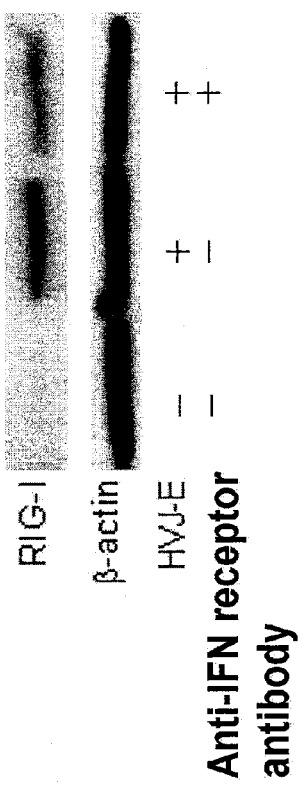

PC3 cells were seeded to a 96-well plate at a density of 5×10⁴ cells/well; 24 hours later, the cells were reacted with the Sendai viral envelope (MOI $10^2$ to $10^4$) and further reacted for 24 hours. The culture supernatant was recovered, and the expression of type I interferons (INF-α and INF-β) was measured by ELISA using a commercially available reagent (PBL Biomedical Laboratories, Piscataway, N.J., USA). The results are shown in FIG. 5(A). Elevations of the expression of IFNα and β were noted Sendai viral envelope dose-dependently. Next, the influences of the Sendai viral envelope and an anti-INF receptor antibody on the expression of the RNA helicase Retinoic Acid Inducible Gene-I (RIG-I) were examined. PC3 cells were seeded to a 96-well plate at a density of $5\times10^5$ cells/well; 24 hours later, the cells were divided by the presence or absence of pretreatment with an anti-IFN receptor antibody (20 μg/ml); after 3-hour pretreatment was performed, the cells were further reacted with the Sendai viral envelope for 24 hours (MOI $10^4$). The results are shown in FIG. 5(B). This finding demonstrated that the treatment with the Sendai viral envelope increased the expression of RIG-I, whereas this action was reduced by the treatment with the anti-IFN receptor antibody.

Example 7

Importance of JAK in Cell Death Induction by Sendai Viral Envelope In Vitro

Figure 6:
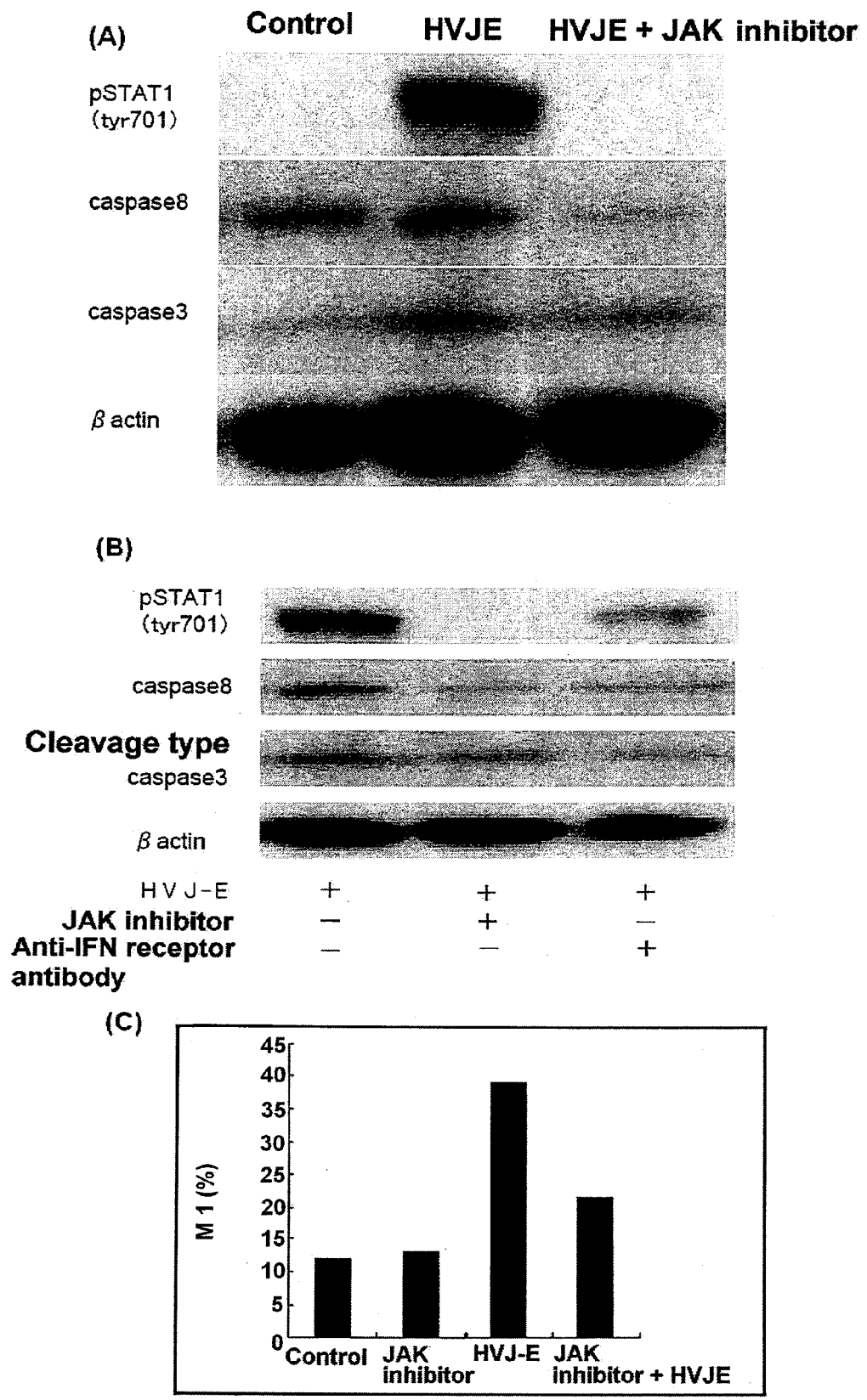
FIG. 6 presents data showing the mechanism behind induction of apoptosis to hormone-refractory prostatic cancer cells PC3 by the Sendai viral envelope. (A) compares the expression of pSTAT1 and caspase proteins in hormone-refractory prostatic cancer cells PC3 treated with the Sendai viral envelope between a JAK inhibitor pretreatment group and a no-treatment group. Used as the internal control was β actin. (B) shows Western blot analysis images comparing the expression of pSTAT1, caspase 3 and caspase 8 proteins in hormone-refractory prostatic cancer cells PC3 treated with the Sendai viral envelope between the presence and absence of JAK inhibitor pretreatment and anti-IFN receptor antibody pretreatment. β actin was used as the internal control. (C) compares annexin V-positive hormone-refractory prostatic cancer cells treated with the Sendai viral envelope between the JAK inhibitor pretreatment group and the no-treatment group.

PC3 cells were seeded to a 6-well plate at a density of about $1\times10^5$ cells/well; 24 hours later, the cells were divided by the presence or absence of 1-hour pretreatment with a JAK inhibitor (1 μM) (Calbiochem, USA), and reacted with the Sendai viral envelope (MOI $10^4$). The cells were further cultured for 24 hours and twice washed with PBS, after which the cells were recovered and lysed with a lysis buffer. After an equal amount of a sample buffer was added thereto, the cell lysate was boiled for 10 minutes. This sample was analyzed for the expression of the proteins pSTAT1 (Ser727: Santa Cruz, Calif., USA), caspase 3 and 8, and β actin (IMG-5142A: IMAGENEX, CA, USA) using the same SDS-PAGE and Western blot method as those in Example. The results are shown in FIG. 6(A). In the group treated with MOI $10^4$ of the Sendai viral envelope, STAT1 phosphorylation and activation of caspase 3 and 8 were noted compared with the control group not treated with the Sendai viral envelop.

To examine the influence of the signal from an IFN receptor, the experiment described below was performed. PC3 cells were seeded to a 6-well plate at a density of about $1\times10^5$ cells/well; 24 hours later, the cells were divided into three groups: those receiving the Sendai viral envelope alone (MOI $10^4$), those receiving the Sendai viral envelope and a JAK inhibitor (1 μM), and those receiving the Sendai viral envelope and an anti-IFN receptor antibody (20 μg/ml); first, pretreatment with the JAK inhibitor and the anti-IFN receptor antibody was performed for 3 hours, after which the cells were further reacted with the Sendai viral envelope for 24 hours (MOI $10^4$). Subsequently, the cells were twice washed with PBS, and the cells were recovered and lysed with a lysis buffer. After an equal amount of a sample buffer was added thereto, the cell lysate was boiled for 10 minutes. This sample was analyzed for the expression of the proteins pSTAT1 (Ser727: Santa Cruz, Calif., USA), caspase 3 and 8, and β actin (IMG-5142A: IMAGENEX, CA, USA) using the same SDS-PAGE and Western blot method as those in Example. The results are shown in FIG. 6(B). When treated with the JAK inhibitor before administration of the Sendai viral envelope, the phosphorylation of STAT1 disappeared, and the expression of caspase 3 and 8 also decreased. When treated with the anti-IFN receptor antibody before administration of the Sendai viral envelope, the phosphorylation of STAT1 decreased, and the expression of caspase 3 and 8 also decreased.

Next, PC3 cells were seeded to a 6-well plate at a density of about $1\times10^5$ cells/well; 24 hours later, the cells were divided by the presence or absence of 1-hour pretreatment with a JAK inhibitor (1 μM), and reacted with the Sendai viral envelope (MOI $10^4$). The cells were further cultured for 24 hours, twice washed with PBS, re-suspended in a staining solution containing annexin V (5 μl) and propidium iodide (PI) (2 μl), treated at room temperature in the dark for 15 minutes, and analyzed using a flow cytometer. The results are shown in FIG. 6(C). Annexin V-positive cells, which had increased with administration of the Sendai viral envelope, decreased as a result of the pretreatment with the JAK inhibitor. These findings demonstrated that the Sendai viral envelope activated the JAK-STAT pathway to activate caspase and induce apoptosis.

Example 8

Analysis using Microarray of Gene Expression Induction by Sendai Viral Envelope

PC3 cells were seeded to 10 cm dishes at a density of $1\times10^6$ cells per dish; 24 hours later, the cells were reacted with the Sendai viral envelope (MOI $10^4$). The cultivation was further continued for 12 hours, and RNA extraction was performed using the RNeasy Mini Kit (Qiagen, Tokyo, Japan) according to the protocol attached to the kit. A microarray analysis was performed using BIO MATRIX RESEARCH INC. (Chiba, Japan). As a result, the top 20 genes ranking in the degree of expression elevation are shown in Table 1. In the table, each underlined gene indicates an IFN-inducing gene.

TABLE 1

| Name of gene | Accession number | Gene code name | Magnification rate |
|---|---|---|---|
| 2'-5-oligoadenylate synthetase-like | NM_003733 | OASL | 46.146305 |
| interferon-induced protein with tetratrico-peptide repeats 1 | NM_001548 | IFIT1 | 29.140244 |
| 2',5'-oligoadenylate synthetase 1 | NM_002534 | OAS1 | 28.13778 |
| myxovirus (influenza virus) resistance 1 | NM_002462 | MX1 | 24.609573 |
| zinc finger CCCH-type | NM_020119 | ZC3HAV1 | 21.645533 |
| 2',5'-oligoadenylate synthetase 1 | NM_016816 | OAS1 | 20.149218 |
| hypothetical protein FLJ20035 | NM_017631 | FLJ20035 | 19.94105 |
| interferon induced with helicase C domain 1 | NM_022168 | IFIH1 | 17.397228 |
| DEAD (Asp-Glu-Ala-Asp) box polypeptide 58 | NM_014314 | DDX58 | 13.773271 |
| dehydrogenase/reductase (SDR family) member 2 | NM_005794 | DHRS2 | 12.704678 |
| interferon-induced protein 44 | NM_006417 | IFI44 | 11.367937 |
| sterile alpha motif domain containing 9 | NM_017654 | SAMD9 | 11.180847 |
| interferon-induced protein with tetratrico-peptide repeats 3 | NM_001549 | IFIT3 | 10.32524 |
| hect domain and RLD 5 | NM_016323 | HERC5 | 9.883629 |
| 2'-5'-oligoadenylate synthetase 2 | NM_016817 | OAS2 | 9.332132 |
| interferon-stimulated transcription factor 3 | NM_006084 | ISGF3G | 8.624724 |
| interferon induced transmembrane protein 1 | NM_003641 | IFITM1 | 8.122226 |
| interferon, alpha-inducible protein 6 | NM_022873 | IFI6 | 6.6947846 |
| hect domain and RLD 6 | NM_017912 | HERC6 | 6.359301 |
| 2'-5'-oligoadenylate synthetase 3 | NM_006187 | OAS3 | 5.908166 |

Example 9

Cancer Cell Proliferation In Vivo

Figure 7:
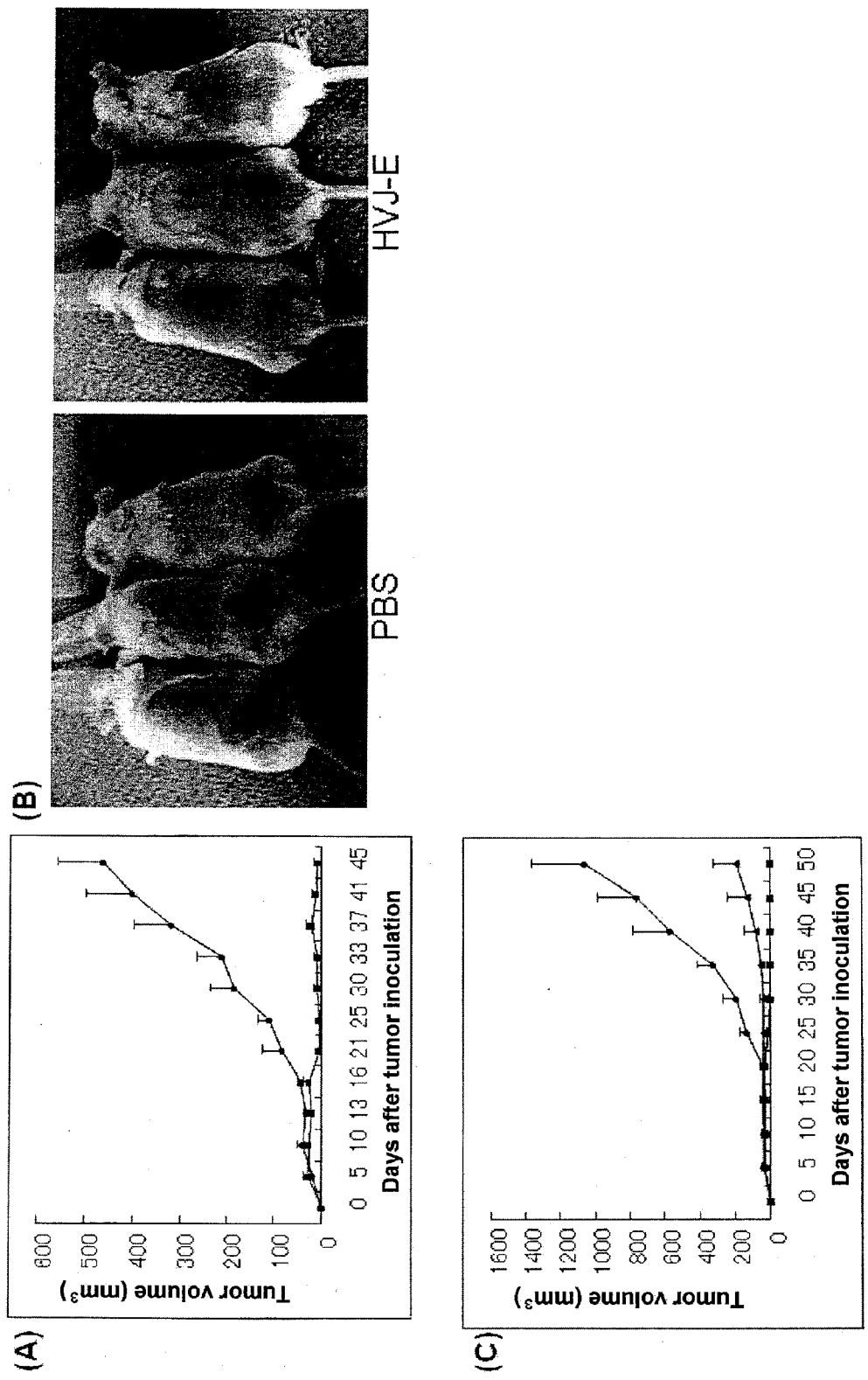
FIG. 7 presents data showing the hormone-refractory prostatic cancer cell regression action of the Sendai viral envelope in vivo. (A) shows that direct administration of the Sendai viral envelope to hormone-refractory prostatic cancer cells transplanted to SCID mice promotes the regression of hormone-refractory prostatic cancer cells. ■: Sendai viral envelope (5,000 HAU) administration group (n=3); ●: PBS administration group (n=3). (B) shows representative photographs of SCID mice in the PBS administration group or the Sendai viral envelope administration group at 41 days after transplantation of hormone-refractory prostatic cancer cells. These findings demonstrated that the Sendai viral envelope exhibited a tumor suppressing effect on hormone-refractory prostatic cancer cells transplanted to SCID mice. (C) shows that direct administration of the Sendai viral envelope to hormone-refractory prostatic cancer cells transplanted to SCID mice deprived of NK cells with an anti-acialo GM-1 antibody promotes the regression of hormone-refractory prostatic cancer cells. ■: Sendai viral envelope (5,000 HAU) administration group (n=3); ●: PBS administration group (n=3); ▲: Sendai viral envelope (5,000 HAU)+anti-acialo GM-1 antibody administration group (n=4). Statistical data are expressed as mean±s.e.m. Group-to-group comparisons were performed by student's t-test. A significance level of P<0.01 was judged to indicate a effect.

The animals used were male 5- to 6-week-old C.B-17/IcrCrj-SCID mice purchased from Charles River Inc. (Yokohama, Japan). PC3 cells ($5 \times 10^6$ cells) were re-suspended in 100 µl of PBS and administered to the back of each male 5- to 6-week-old C.B-17/IcrCrj-SCID mouse by intradermal injection. When the cancer grew up to a diameter of about 4-6 mm, at 10, 13, and 16 days after surgery, the Sendai viral envelope (5,000 HAU in a total volume of 100 ml) or 100 µl of PBS was injected into the tumor. Cancer volumes were measured by blind testing using calipers, and calculations were made using the following formula: tumor volume ($mm^3$)=length×(width)$^2$/2. The results are shown in FIG. 7(A). Tumor growth was remarkably inhibited in the Sendai viral envelope group; in the control PBS group, however, this effect was not noted. Photographs of the Sendai viral envelope treatment group and the PBS treatment group at 41 days after tumor transplantation are shown in FIG. 7(B). These findings demonstrated that the Sendai viral envelope had a tumor suppressing effect on the hormone-refractory prostatic cancer cells transplanted to the SCID mice.

In an NK cell-deficient model generated by administering an anti-acialo GM-1 antibody, the effect of the Sendai viral envelope was examined. PC3 cells were intradermally injected to the back of a syngeneic SCID mouse, and the Sendai viral envelope alone, or the Sendai viral envelope and 40 µl of acialo GM1 antibody, were injected into tumors three times at 3-day intervals (days 10, 13, and 16). The results of this experiment are shown in FIG. 7(C). In the group treated with the Sendai viral envelope and the anti-acialo GM1 antibody, a reduction in the tumor suppressing effect was observed.

Figure 8:
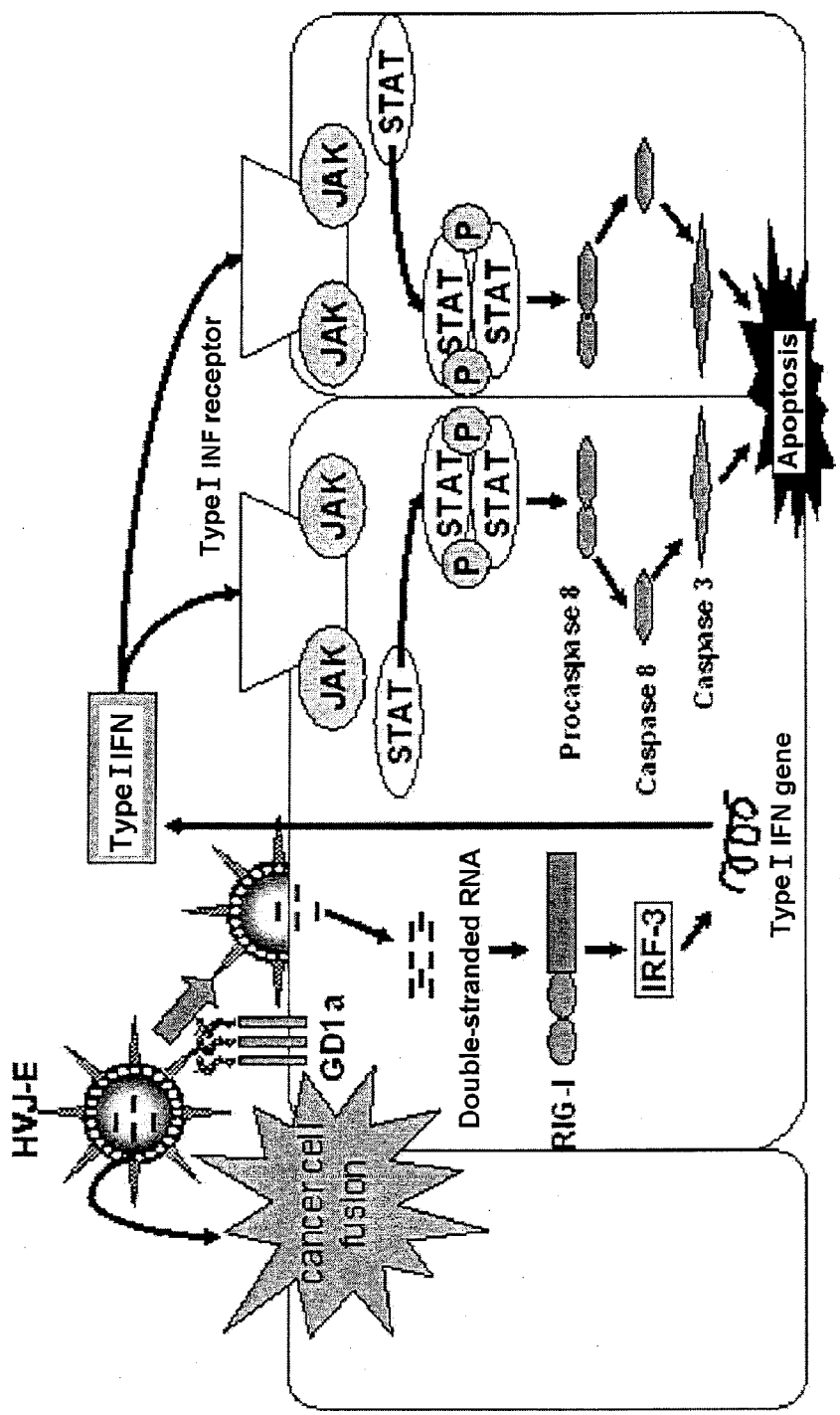
FIG. 8 is a drawing showing the mechanism behind apoptosis via interferons to hormone-refractory prostatic cancer cells by the Sendai viral envelope.

An outline of the mechanism behind the induction of apoptosis to non-hormone-refractory prostatic cancer cells by the Sendai viral envelope, estimated from the above, is shown in FIG. 8. It has already been known that the ganglioside GD1a (Rocheleau J. V. et al., Biosci Rep. 20, 139-55, 2000, Wybenga L. E et al., Biochemistry 35, 9513-8, 1996), which serves as a receptor of the Sendai viral envelope, is highly expressed in PC3 cells and DU145 cells, but not expressed in LNCap cells (Ravindranath M. H et al., Int J Cancer. 116, 368-77. 2005).

Example 10

Tumor Growth Suppressing Effect of GEN0101 in Mouse Model of Transplantation of Human PC-3 Cell Line An experiment using a freeze-dried preparation of the Sendai viral envelope prepared with human cells (HEK293) as the host (GEN0101) was performed. The method was basically the same as the method using chicken eggs, except that human cells (HEK293) were used as the host in place of chicken eggs. After purification, the freeze-dried preparation obtained by a conventional method was used. For this preparation, neuraminidase activity (mNAU) was used as the unit of measurement for the Sendai viral envelope (the conversion of HAU and mNAU was approximately HAU/mNAU=5 to 3).

Tumor growth suppressing effects on a cancer-bearing animal model developed by intradermally transplanting a hormone-refractory human prostatic cancer cell line (PC3) to an SCID mouse were investigated under two conditions: GEN0101 (1,000 mNAU) administered into tumors a total of 3 times at 4-day intervals (Test-a), and administered into tumors a total of 2 times at 7-day intervals (Test-b). On the starting day of experiment (Day 0), human PC3 cells in the logarithmic growth phase were trypsinized and washed with RPMI1640 (Invitrogen Japan K.K.), after which the cells were dispersed in a 2:1 mixed liquid of RPMI1640 and Matrigel (Nippon Becton Dickinson Co., Ltd.) to prepare a cell suspension for transplantation. Twenty-six 6-week-old male C.B-17/lcr-scid/scid Jcl mice (CLEA Japan, Inc.) under Nembutal (Dainippon Sumitomo Pharma Co., Ltd.) anesthesia had the hair in the right back shaven with clippers, and $2.0 \times 10^6$ cells per animal were transplanted intradermally. Four days after tumor cell transplantation (day 4), 20 animals were selected, divided into four groups by stratified random sampling so that the mean tumor volume became nearly uniform among the groups, and further randomly allocated to medication groups in Test-a and -b (GEN0101) and a control group (solvent dosing group) (n=5). Administration of 1,000 mNAU of GEN0101 or a solvent (5% trehalose solution) took place a total of three times on day 4, day 8 and day 12 for test-A, and a total of two times on day 4 and day 11 after cell transplantation for test-B. On each administration day, animals were placed in an anesthesia box filled with Forane (ABBOTT JAPAN Co., Ltd.) vaporized using an anesthetic vaporizer for a specified time. 0.1 mL of GEN0101 or the solvent alone was administered into the tumor of each animal just after being taken out from the anesthesia box, using a 1-mL syringe (Terumo Corporation) and a 30G injection needle (Nippon Becton Dickinson Co., Ltd.). Between the starting day of medication and the final day of experiment (Day 48), tumor volumes and body weight change rates were monitored.

Tumor volumes and body weight change rates were calculated using the equation below.

Tumor volume ($mm^3$)=[minor diameter (mm)]$^2$×major diameter (mm)/2

Body weight change rate (%)=100×[(body weight on each measuring day/body weight at time of grouping)−1]

The parameter for drug effect evaluation was tumor volume on day 48; differences between the control group and the medication group were statistically tested. In both Tests-a and -b, first, homoscedasticity was tested by F-test; in case of equal variances, Student's t test was performed, and in case of unequal variances, Welch's t-test was performed. All the tests were performed as a two-tailed test, the significance level being set at a=0.05 or a=0.01.

Figure 9:
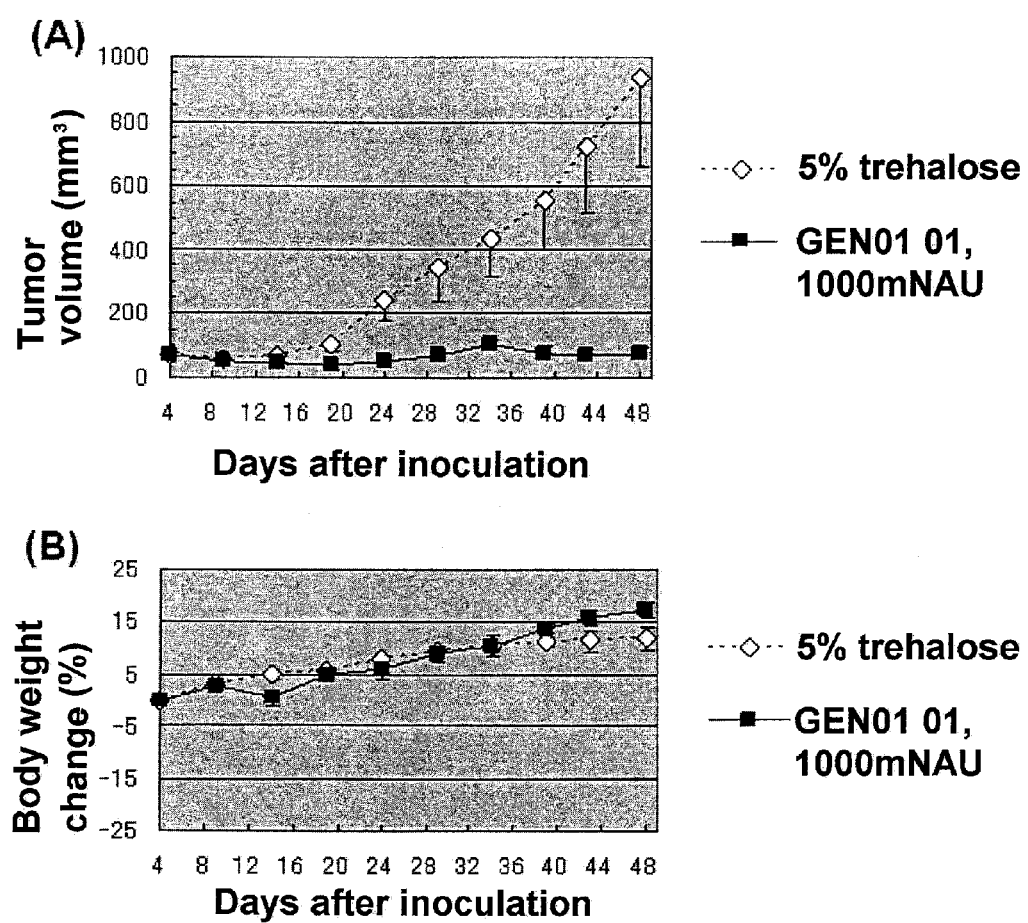
FIG. 9(A) shows the tumor growth suppressing effect of a total of 3 times of administration of GEN0101 at 4-day intervals in a mouse model of transplantation of a human PC3 cell line. (B) shows changes over time in body weight change rate after the start of administration of GEN0101 in the mouse model of transplantation of the human PC3 cell line.
Figure 10:
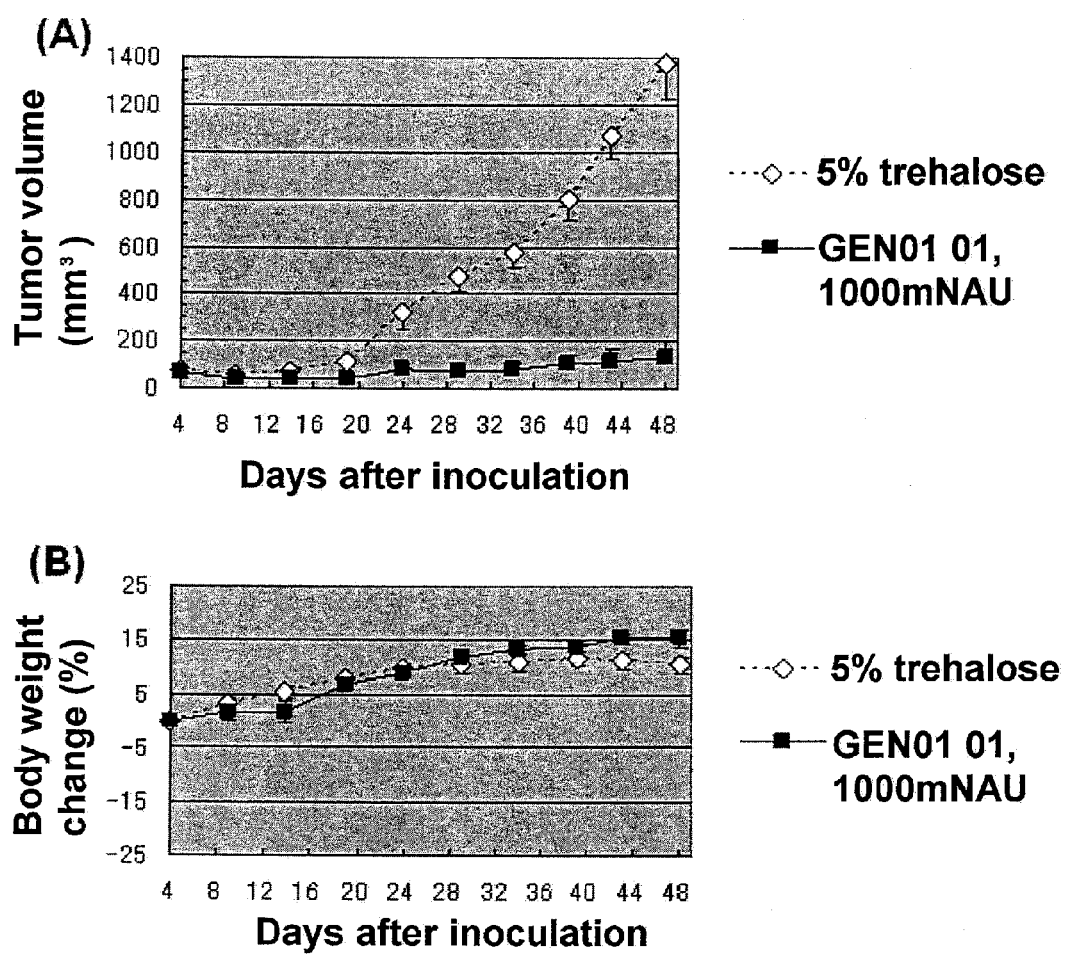
FIG. 10(A) shows the tumor growth suppressing effect of a total of 2 times of administration of GEN0101 at 7-day intervals in a mouse model of transplantation of a human PC3 cell line. (B) shows changes over time in body weight change rate in the mouse model of transplantation of the human PC3 cell line after the start of administration of GEN0101.

Changes over time from the starting day of medication (day 4) to day 48 in the means and standard errors of tumor volume and body weight change rate are shown by test group in FIG. 9 for Test-a and FIG. 10 for Test-b. In both Test-a and Test-b, after Day 19, the mean tumor volume increased remarkably in the control group, whereas in the medication group, no clear increasing tendency was seen, and the volume was low throughout the observation period (FIG. 9A, FIG. 10A). As of the day of examination completion (day 48), some individuals were seen in which the tumor was not readily identifiable by visual inspection in the medication group (data not shown). The mean tumor volume for the medication group on Day 48 was 8.0% compared with the control group for Test-a, and 9.5% compared with the control group for Test-b; in both tests, the difference between the control group and the administration group was statistically significant (p<0.05 [Test-a], p<0.01 [Test-b]). In all tests, throughout the observation period, almost no influence of the medication on body weight gain was noted (FIG. 9B, FIG. 10B).

These findings demonstrated a significant drug effect in both regimens: 1,000 mNAU of GEN0101 administered into tumors a total of 3 times at a 4-day interval from 4 days after tumor transplantation (day 4), and administered into tumors a total of 2 times at 7-day intervals from day 4. It was also demonstrated that almost no influence of the medication on body weight gain was noted.

Example 11

Tumor Growth Suppressing Effect of HVJ-E in Mouse Model of Transplantation of Mouse Melanoma B16/BL6 Cell Line (1) Test Substance and Control Substance Used as the test substance was a freeze-dried preparation of HVJ-E (Genomidea Inc., lot number: CC7-13). In the administration, the freeze-dried preparation was dissolved in water for injection (Otsuka Pharmaceutical Factory, Inc., lot number: K7C75) to 40000 HAU/mL, after which the solution was diluted with 5% trehalose solution (Genomidea Inc., lot number: GP29) to obtain a final concentration of 400 HAU/mL or 4000 HAU/mL, and these were designated DFD-40 and DFD-400, respectively. The test substance was prepared on the day of administration and stored on ice, after which it was filled in an injection syringe and allowed to stand at normal temperature for 1 minute until administration. Used as the control substance was 5% trehalose solution (Genomidea Inc., lot number: GP29). Hereinafter, the 5% trehalose solution is denoted TS.

(2) Animals

Seventy 6-week-old female C57BL/6J mice, as animals for transplantation of the B16/BL6 cell line, were purchased from Charles River Japan Inc., and individually identified by the ear punching method. Written on breeding cage labels were the day of animal receipt, strain, sex, and individual identification number before grouping, and study number, the day of animal receipt, strain, sex, test group, animal number, and individual identification number after grouping. The acclimation period was 8 days long from the day of animal receipt; during the acclimation period, all individuals were examined for gross findings (presence or absence of external abnormalities, food consumption/water consumption statuses and the like). Autoclaved bedding (Iwakura Corporation) was placed in mouse cages of polycarbonate (CLEA Japan, Inc., 13.6 long×20.8 wide×11.5 cm high), and one mouse per cage was housed during both the acclimation period and the experimental period. The breeding room was kept at a temperature of 23±2° C., a humidity of 55±10%, a ventilation frequency of 10 to 15 times/hour (all-fresh-air system), and a lighting time of 7:00 to 19:00. The racks housing the cages were wiped with a disinfectant solution (a 300-fold dilution of PURELOX (6% sodium hypochlorite, OYALOX Co., Ltd.)) every day except on Saturdays, Sundays and national holidays, with the floor wiped with the disinfectant solution after cleaning. The feed was a solid food (CRF-1, Oriental Yeast Co., Ltd.), and the drinking water was Ritto City municipal tap water. The remaining animals were removed from the study and euthanized with diethyl ether.

(3) Cultivation of Tumor Cell Line and Preparation of Cell Suspension

B16/BL6 (mouse melanoma line, ID: TKG 0598, lot number: 12-6-02) was purchased from the Cell Research Center for Biomedical Research, Institute of Development, Aging and Cancer, Tohoku University, and used within 1 month after 1 week of the start of resurgence culture. Using an RPMI1640 (Invitrogen Japan K.K.) containing 10% fetal bovine serum (JRH Biosciences Company) as the passage medium, the cells were cultured in the presence of 5% $CO_2$ at 37° C. In case of passage at 2-day intervals, $1.5 \times 10^6$ cells were seeded to a 10 cm culture dish. In case of passage at 3-day intervals, $1.0 \times 10^6$ cells were seeded to a 10 cm culture dish. In the afternoon of the starting day of experiment (Day 0), cells in the logarithmic growth phase were trypsinized and suspended in phosphate-buffered physiological saline (PBS(−), Nissui Pharmaceutical Co., Ltd.) to $5.0 \times 10^6$ cells/mL ($5.0 \times 10^5$ cells/0.1 mL/mouse). The liquid obtained was used as the cell suspension for transplantation, which was collected into a 1 mL injection syringe (Terumo Corporation) equipped with a 30G injection needle (Becton Dickinson Company), and transplanted. After being prepared, the cell suspension was placed on ice, and transplantation was completed within 60 minutes with vigorous stirring given by pipetting operation whenever appropriate.

(4) Transplantation of Tumor Cells

Pentobarbital sodium (Nembutal Injection, Dainippon Sumitomo Pharma Co., Ltd.) was diluted with physiological saline (Otsuka Pharmaceutical Factory, Inc.) to obtain a 6 mg/mL solution. Each mouse was anesthetized by intraperitoneally administering this solution at a dose of 60 mg/kg of pentobarbital sodium. The hair at the transplantation site was shaven with clippers, after which 0.1 mL of the cell suspension was intradermally transplanted to the right back.

(5) Grouping

Four days after the tumor cell transplantation (Day 4), tumor diameters were measured. Individuals with a tumor volume of 70 mm$^3$ or more, individuals with a leakage of the cell suspension occurring at the time of the tumor cell transplantation, individuals with a black spot found under the skin in the vicinity of the tumor cell transplantation site, and individuals with an erythema at the tumor cell transplantation site were removed; the mean and standard deviation (SD) of tumor volume for all remaining individuals were calculated. Next, 54 animals meeting the requirement of a tumor volume within mean±2SD were determined. These individuals were divided into six groups by tumor volume by stratified random sampling so that the mean tumor volume became uniform among the groups. Furthermore, the animals were further randomly allocated to various test groups of 9 animals using cards.

Eleven days after the tumor cell transplantation (Day 11), an nonnegligible bias of tumor volume was noted among the groups; before administration on Day 11, on the basis of tumor volume on Day 11, grouping was performed again. Eighteen individual animals receiving the same substance (test groups 1 and 4, test groups 2 and 5, test groups 3 and 6) were divided into two groups by tumor volume by stratified random sampling so that the mean volume became nearly uniform, and the animals in each of the two groups were further randomly allocated to six groups for 3-time administration or 6-time administration using cards. Particulars of the grouping are shown in Table 2.

TABLE 2

| Group | Description | Substance administered | Dose (HAU/mouse) | Dosing frequency (times) | Route of administration | Number of animals |
|---|---|---|---|---|---|---|
| A | 3-time administration control group | TS | — | 3 | Intratumor | 9 |
| B | 3-time administration 40 HAU group | DFD-40 | 40 | 3 | Intratumor | 9 |

TABLE 2-continued

| Group | Description | Substance administered | Dose (HAU/mouse) | Dosing frequency (times) | Route of administration | Number of animals |
|---|---|---|---|---|---|---|
| C | 3-time administration 400 HAU group | DFD-400 | 400 | 3 | Intratumor | 9 |
| D | 6-time administration control group | TS | — | 6 | Intratumor | 9 |
| E | 6-time administration 40 HAU group | DFD-40 | 40 | 6 | Intratumor | 9 |
| F | 6-time administration 400 HAU group | DFD-400 | 400 | 6 | Intratumor | 9 |

(6) Administration of Test Substance and Control Substance

At 4 days (Day 4), 6 days (Day 6), 8 days (Day 8), 11 days (Day 11), 13 days (Day 13) and 15 days (Day 15) after tumor cell transplantation, the test substance or control substance was administered. At 11 days (Day 11), 13 days (Day 13) and 15 days (Day 15), administration took place for Group D, Group E, and Group F only. Animals were placed in an anesthesia box wherein 2 to 3% isoflurane (Forane, ABBOTT JAPAN Co., Ltd.) was maintained using a vaporizer (TK-5, NeuroScience, Inc.), and anesthetized by inhalation for 6 minutes. Just after each animal was taken out from the anesthesia box, 0.1 mL of the test substance or control substance was administered into the tumor of each animal. In the administration, an injection needle was stabbed under the skin in the vicinity of the tumor mass, and the reach of the needle tip to the tumor through below the skin was confirmed, after which the needle was further stabbed into the center of the tumor. The test substance or control substance was administered slowly while feeling resistance until the end of the administration. However, in individuals wherein the tumor diameter exceeded 160 mm$^3$ after administration on Day 11 (4th time), the test substance or control substance was administered to the marginal portion of the tumor, where tumor tissue was likely to be surviving.

(7) Measurement of Tumor Volumes

On Days 4, 8, 11, 13, 15, 18, 20, 24, 28, 32 and 36, the minor diameter and major diameter of the tumor were measured using digital callipers (Mitutoyo Corporation, CD-15). In measuring the tumor diameters, the three-item criteria shown below were followed. (1) The black spot or black node at the tumor cell transplantation site should be measured. (2) If a crust or the like is observed, the site, if black and in contact with the primary focus, should be included in the measuring range. (3) If the primary focus is no longer black, the tumor should be judged to have disappeared. The tumor volume of each animal in each group was calculated using the following calculation equation.

Tumor volume (mm$^3$)=[minor diameter (mm)]$^2$×major diameter (mm)/2

Figure 11:
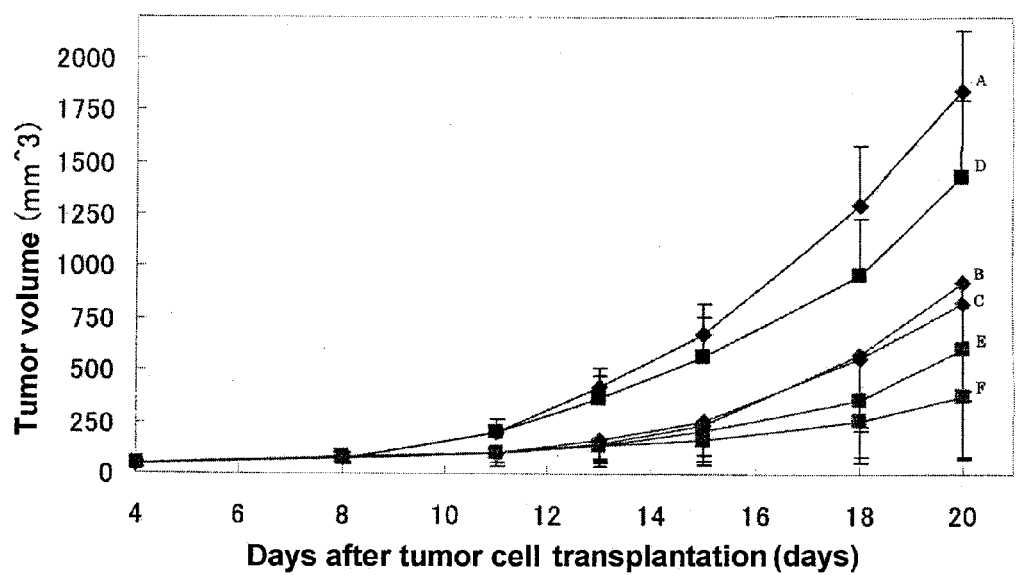
FIG. 11 shows changes in tumor volume in each group after administration of HVJ-E into tumors. ▲$^A$: Group A (3-time administration control group), ▲$^B$: Group B (3-time administration 40 HAU group), ▲$^C$: Group C (3-time administration 400 HAU group), ■$^D$: Group D (6-time administration control group), ■$^E$: Group E (6-time administration 40 HAU group), ■$^F$: Group F (6-time administration 400 HAU group), mean±standard deviation for 6 to 9 animals, **: $p<0.01$, Dunnett's multiple comparison test at 20 days after tumor cell transplantation.

Statistical analysis was performed on tumor volume on Day 20. Day 20 was set as the upper limit for the period when the tumor did not influence body weight. The statistical analysis took place using the GraphPad PRISM 4 (GraphPad Software Company). The results obtained on Day 20 were analyzed by dosing frequency using Dunnett's multiple comparison test. Specifically, the results for Group B (3-time administration 40 HAU group) and Group C (3-time administration 400 HAU group) versus the results for Group A (3-time administration control group), and the results for Group E (6-time administration 40 HAU group) and Group F (6-time administration 400 HAU group) versus the results for Group D (6-time administration control group) were tested respectively. If the test was significant, differences related to dosing frequency were analyzed by Holm's multiple comparison test for the combinations Group A and Group D, Group B and Group E, and Group C and Group F. Also, differences related to dose were analyzed by Holm's multiple comparison test for the combinations Group B and Group C and Group E and Group F. Tumor volumes after intratumoral administration of HVJ-E are shown in FIG. 11. In all of Group B, Group C, Group E, and Group F, tumor volumes were lower than in control groups with corresponding dosing frequencies; at 20 days after the tumor cell transplantation, tumor volumes were significantly lower than in control groups with corresponding dosing frequencies. Meanwhile, both with 3-time administration and with 6-time administration, no difference was noted between the 40 HAU group and the 400 HAU group. At both the 40 HAU and 400 HAU doses, no difference was noted between the 3-time administration group and the 6-time administration group. The results of the tests are given together in Table 3.

TABLE 3

| Comparison of 3-time administration and 6-time administration | |
|---|---|
| Group A and Group D | NS |
| Group B and Group E | NS |
| Group C and Group F | NS |
| Comparison of 40 HAU and 400 HAU | |
| Group B and Group C | NS |
| Group E and Group F | NS |

NS: Not significant, Holm's multiple comparison test on tumor volume at 20 days after tumor cell transplantation (8) Calculation of Survival Rates For each group, the survival rate until the day of completion of experiment was calculated using the following calculation equation. Regarding the dates of death, deaths before noon were regarded as occurring on the day, and deaths thereafter were regarded as occurring on the following day. For statistical analysis, graphs of survival rate were generated by the Kaplan-Meier method, after which data were analyzed by dosing frequency using the Logrank test. Multiple corrections were performed according to the Holm method. Survival rates were calculated according to the equation below.

Survival rate (%)=100×(number of surviving animals in each group)/(number of animals in each group on Day 11)

Figure 12:
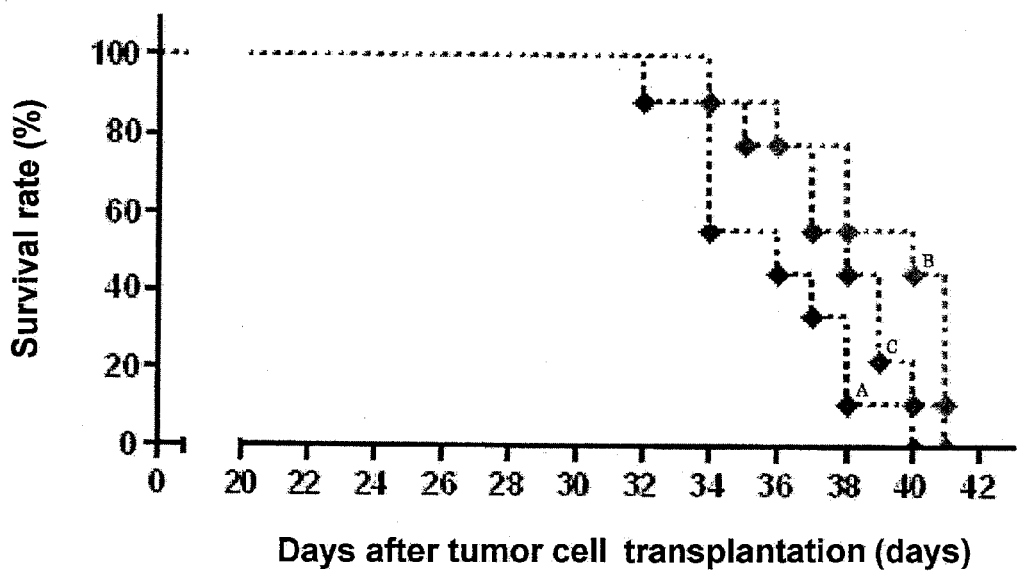
FIG. 12 shows the survival curves for various groups after administration of HVJ-E into tumors. A: Survival curves for the groups receiving 3-time administration. B: Survival curves for the groups receiving 6-time administration. ▲$^A$: Group A (3-time administration control group), ▲$^B$: Group B (3-time administration 40 HAU group), ▲$^C$: Group C (3-time administration 400 HAU group), ■$^D$: Group D (6-time administration control group), ■$^E$: Group E (6-time administration 40 HAU group), ■$^F$: Group F (6-time administration 400 HAU group)
Figure 12:
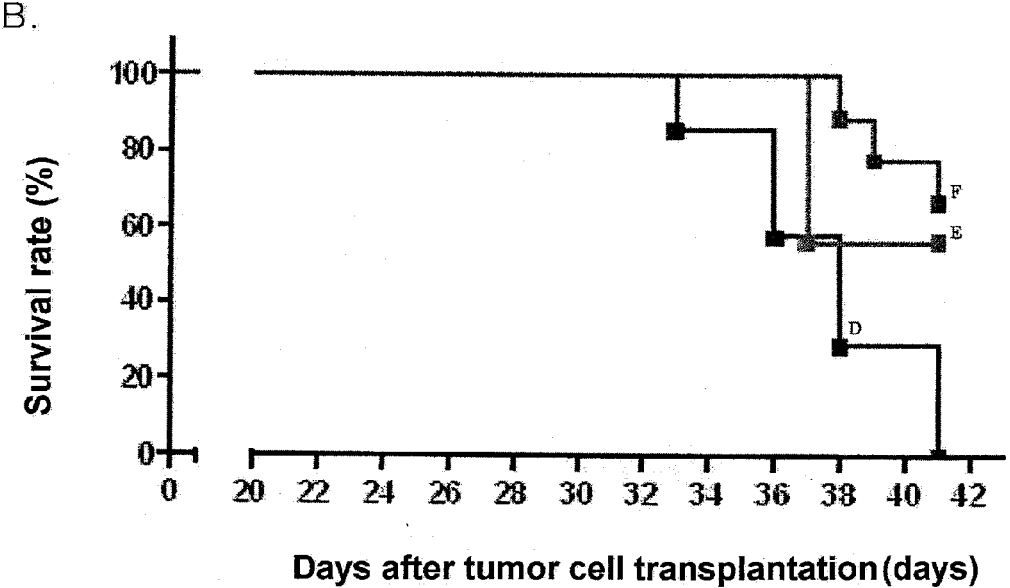

In Group D only, two individuals died within 1 day after 5th administration. Although the causes of these deaths could not be identified, it is possible that stress due to administration of the drug liquid in the expanded tumor might cause a lethal reaction like shock. The data on the two deceased individuals were excluded from the analysis. Survival curves after intratumoral administration of HVJ-E are shown in FIG. 12. With 3-time administration, in Group C (400 HAU group), compared with the control group, no extension of the survival period was noted, and in Group B (40 HAU group), a significant extension of the survival period was noted. Meanwhile, with 6-time administration, in both Group E (40 HAU group) and Group F (400 HAU group), a significant extension of the survival period was noted, compared with the control group. The results of Logrank test are shown in Table 4.

TABLE 4

| 3-time administration | |
|---|---|
| Group B (40 HAU) | * |
| Group C (400 HAU) | NS |

| 6-time administration | |
|---|---|
| Group E (40 HAU) | * |
| Group F (400 HAU) | ** |

NS: Not significant,
*: p < 0.05,
**: p < 0.01

Logrank test versus control group at the time all animals in the control group have died Judging from the above, the survival period extended in all groups. In this Example, no significant difference was noted in the 400 HAU 3-time administration group (Group C), but in the other groups, a significant difference was noted.

(9) Body Weight

Each animal was weighed using an electronic balance ((Kensei Co., Ltd.), GX-2000) on the day after animal receipt (Day-7), the day of tumor cell transplantation (Day 0), and the day of tumor volume measurement (Days 4, 8, 11, 15, 18, 20, 24, 28, 32 and 36). The measured results were printed using a printer (A & D Co., Ltd., AD-8121). For each group, body weight change rates for individual animals after Day 4 were calculated using the following calculation equation.

Body weight change rate (%)=100×(body weight on each measuring day−body weight on Day 4)/(body weight on Day 4)

Figure 13:
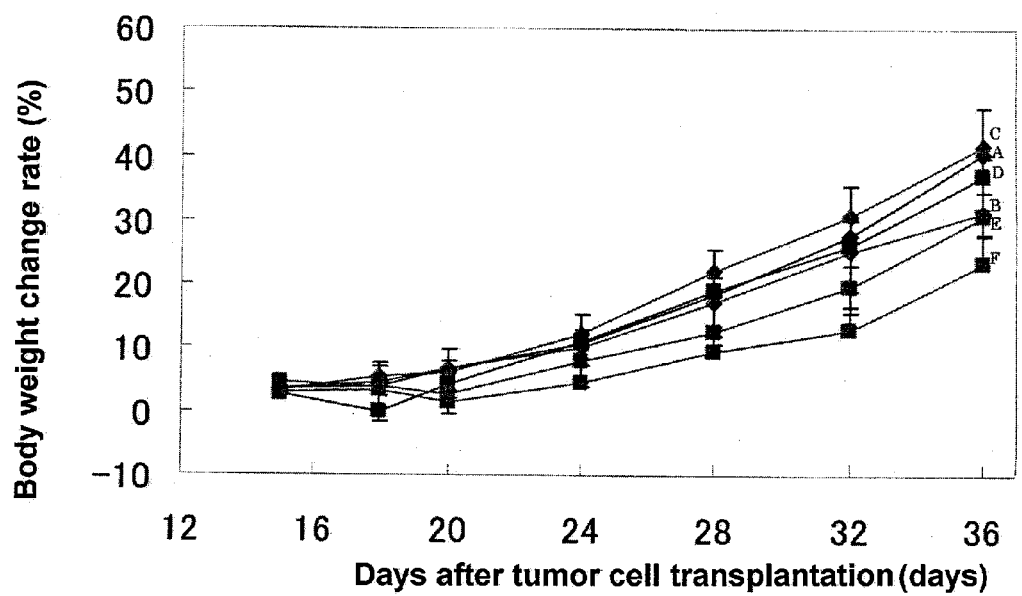
FIG. 13 shows body weight change rates from day 15 to day 36 various groups. ▲$^A$: Group A (3-time administration control group), ▲$^B$: Group B (3-time administration 40 HAU group), ▲$^C$: Group C (3-time administration 400 HAU group), ■$^D$: Group D (6-time administration control group), ■$^E$: Group E (6-time administration 40 HAU group), ■$^F$: Group F (6-time administration 400 HAU group); data are shown as the mean±standard deviation of change rate (%) with the body weight on day 4 as the reference.

Regarding the body weight change rates from Day 4 (initial grouping) to Day 11, all groups had some individuals experiencing a transient body weight loss; however, judging from the mean body weight change rate, no remarkable body weight gain or loss was observed as an overall tendency, nor was there any noticeable difference among the groups. As for the body weight change rates after Day 12, no remarkable increase or decrease in body weight was noted until Day 20, nor was there any noticeable difference among the groups. After Day 20, in all groups, the mean body weight change rate increased, and a tendency for body weight gain was seen throughout the experimental period. Shown in FIG. 13 are the body weight change rates from Day 15 to Day 36 in the respective groups.

INDUSTRIAL APPLICABILITY

In the treatment of prostatic cancers, PSA screening, surgical resection, endocrine therapy, radiotherapy and the like are currently available, but their radical treatment remains a major problem. The cancer therapeutic/prophylactic agent containing a viral envelope, particularly the Sendai viral envelope, as an active ingredient, provided by the present invention, exhibits an excellent therapeutic/prophylactic effect on hormone-refractory prostatic cancers, and is therapeutically effective particularly on recurring prostatic cancers after endocrine therapy. The cancer therapeutic/prophylactic agent of the present invention containing the Sendai viral envelope alone exhibits a regression effect on melanoma at low doses, and is expected as a new therapeutic drug that will contribute to reducing the burden on the patient.

This application is based on a patent application No. 2008-237102 filed in Japan (filing date: Sep. 16, 2008), the contents of which are incorporated in full herein.

The invention claimed is:

1. A method of treating prostatic cancer, comprising administering to an individual in need thereof an effective amount of a wild-type Sendai virus envelope to a prostatic cancer patient, wherein the patient has a history of receiving endocrine therapy and bears a prostatic cancer whose androgen susceptibility has been partially or completely reduced.

2. The method of claim 1 wherein the viral envelope is administered directly to the prostatic cancer.

3. The method of claim 1 wherein the viral envelope is injected directly to the prostatic cancer.

4. The method of claim 1 further comprising administering a second cancer therapeutic method.

5. The method of claim 4 wherein the second cancer therapeutic method is selected from the group consisting of medication, endocrine therapy, radiotherapy, chemotherapy and immunotherapy.

6. The method of claim 1, wherein the prostatic cancer patient having a history of receiving endocrine therapy bears a hormone-refractory prostatic cancer.

7. The method of claim 1, wherein the wild-type Sendai virus envelope is from an inactivated wild-type Sendai virus envelope.

8. The method of claim 6, wherein the hormone-refractory prostatic cancer is the prostatic cancer expressing GD1a.

9. The method of claim 1, wherein the Sendai virus envelope is empty.

* * * * *

UNITED STATES PATENT AND TRADEMARK OFFICE
CERTIFICATE OF CORRECTION

PATENT NO.        : 8,691,212 B2                                        Page 1 of 1
APPLICATION NO.   : 13/119148
DATED             : April 8, 2014
INVENTOR(S)       : Kaneda et al.

It is certified that error appears in the above-identified patent and that said Letters Patent is hereby corrected as shown below:

IN THE SPECIFICATION

Column 7, line 2:

Delete "▲$^A$" and insert --◆$^A$--.

Column 7, line 3:

Delete "▲$^B$" and insert --◆$^B$--.

Column 7, line 4:

Delete "▲$^C$" and insert --◆$^C$--.

Column 7, line 14:

Delete "▲$^A$" and insert --◆$^A$--.

Column 7, line 15:

Delete "▲$^B$" and insert --◆$^B$--.

Column 7, line 16:

Delete "▲$^C$" and insert --◆$^C$--.

Column 7, line 22:

Delete "▲$^A$" and insert --◆$^A$--.

Column 7, line 23:

Delete "▲$^B$" and insert --◆$^B$--.

Column 7, line 24:

Delete "▲$^C$" and insert --◆$^C$--.

Signed and Sealed this
Twenty-seventh Day of October, 2015

Michelle K. Lee
*Director of the United States Patent and Trademark Office*